(12) United States Patent
Gall

(10) Patent No.: US 7,728,311 B2
(45) Date of Patent: Jun. 1, 2010

(54) CHARGED PARTICLE RADIATION THERAPY

(75) Inventor: Kenneth Gall, Harvard, MA (US)

(73) Assignee: Still River Systems Incorporated, Littleton, MA (US)

(*) Notice: Subject to any disclaimer, the term of this patent is extended or adjusted under 35 U.S.C. 154(b) by 0 days.

(21) Appl. No.: 11/601,056

(22) Filed: Nov. 17, 2006

(65) Prior Publication Data

US 2008/0093567 A1   Apr. 24, 2008

Related U.S. Application Data

(60) Provisional application No. 60/738,404, filed on Nov. 18, 2005.

(51) Int. Cl.
*H01J 37/08* (2006.01)
*H01F 6/00* (2006.01)

(52) U.S. Cl. ............... 250/492.21; 250/492.1; 250/493.1; 250/396 R; 335/216

(58) Field of Classification Search ............ 250/492.3, 250/505.1, 306, 396 R
See application file for complete search history.

(56) References Cited

U.S. PATENT DOCUMENTS

| | | | |
|---|---|---|---|
| 2,615,129 A | 10/1952 | McMillan | |
| 3,175,131 A | 3/1965 | Burleigh et al. | |
| 3,432,721 A | 3/1969 | Naydan et al. | |
| 3,679,899 A | 7/1972 | Dimeff | |
| 3,689,847 A | 9/1972 | Verster | |
| 3,868,522 A | 2/1975 | Bigham et al. | |
| 3,925,676 A | 12/1975 | Bigham et al. | |
| 3,958,327 A | 5/1976 | Marancik et al. | |
| 3,992,625 A | 11/1976 | Schmidt et al. | |
| 4,038,622 A | 7/1977 | Purcell | |
| 4,047,068 A | 9/1977 | Ress et al. | |
| 4,112,306 A | 9/1978 | Nunan | |
| 4,129,784 A | 12/1978 | Tschunt et al. | |

(Continued)

FOREIGN PATENT DOCUMENTS

DE    2753397    6/1978

(Continued)

OTHER PUBLICATIONS

PCT International Preliminary Report on Patentability of corresponding PCT application No. PCT/US2006/044853, mailed May 29, 2008 (8 pages).

(Continued)

*Primary Examiner*—Robert Kim
*Assistant Examiner*—Johnnie L Smith, II
(74) *Attorney, Agent, or Firm*—Fish & Richardson P.C.

(57) ABSTRACT

Among other things, an accelerator is mounted on a gantry to enable the accelerator to move through a range of positions around a patient on a patient support. The accelerator is configured to produce a proton or ion beam having an energy level sufficient to reach any arbitrary target in the patient from positions within the range. The proton or ion beam passes essentially directly from the accelerator to the patient. In some examples, the synchrocyclotron has a superconducting electromagnetic structure that generates a field strength of at least 6 Tesla, produces a beam of particles having an energy level of at least 150 MeV, has a volume no larger than 4.5 cubic meters, and has a weight less than 30 Tons.

39 Claims, 11 Drawing Sheets

U.S. PATENT DOCUMENTS

| | | |
|---|---|---|
| 4,139,777 A | 2/1979 | Rautenbach |
| 4,197,510 A | 4/1980 | Szu |
| 4,220,866 A | 9/1980 | Symmons et al. |
| 4,336,505 A | 6/1982 | Meyer |
| 4,345,210 A | 8/1982 | Tran |
| 4,353,033 A | 10/1982 | Kurasawa |
| 4,507,614 A | 3/1985 | Prono et al. |
| 4,507,616 A * | 3/1985 | Blosser et al. .............. 315/502 |
| 4,589,126 A | 5/1986 | Augustsson et al. |
| 4,633,125 A | 12/1986 | Blosser et al. |
| 4,641,057 A * | 2/1987 | Blosser et al. ................ 313/62 |
| 4,641,104 A | 2/1987 | Blosser et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A * | 6/1988 | Maughan et al. ......... 250/505.1 |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,902,993 A | 2/1990 | Krevent |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,987,309 A | 1/1991 | Klasen et al. |
| 4,996,496 A | 2/1991 | Kitamura et al. |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,072,123 A | 12/1991 | Johnsen |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,166,531 A | 11/1992 | Huntzinger |
| 5,189,687 A * | 2/1993 | Bova et al. .................... 378/65 |
| 5,240,218 A | 8/1993 | Dye |
| 5,260,581 A | 11/1993 | Lesyna et al. |
| 5,278,533 A | 1/1994 | Kawaguchi |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,405,235 A | 4/1995 | Lebre et al. |
| 5,440,133 A | 8/1995 | Moyers et al. |
| 5,461,773 A | 10/1995 | Kawaguchi |
| 5,463,291 A | 10/1995 | Carroll et al. |
| 5,511,549 A | 4/1996 | Legg et al. |
| 5,521,469 A | 5/1996 | Laisne |
| 5,585,642 A | 12/1996 | Britton et al. |
| 5,668,371 A | 9/1997 | Deasy et al. |
| 5,726,448 A | 3/1998 | Smith et al. |
| 5,778,047 A | 7/1998 | Mansfield et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,993,373 A | 11/1999 | Nonaka et al. |
| 6,034,377 A | 3/2000 | Pu |
| 6,057,655 A | 5/2000 | Jongen |
| 6,061,426 A | 5/2000 | Linders et al. |
| 6,094,760 A | 8/2000 | Nonaka et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,316,776 B1 | 11/2001 | Hiramoto et al. |
| 6,433,336 B1 | 8/2002 | Jongen et al. |
| 6,433,349 B2 | 8/2002 | Akiyama et al. |
| 6,441,569 B1 | 8/2002 | Janzow |
| 6,443,349 B1 | 9/2002 | Van Der Burg |
| 6,476,403 B1 | 11/2002 | Dolinskii et al. |
| 6,492,922 B1 | 12/2002 | New |
| 6,501,981 B1 | 12/2002 | Schweikard et al. |
| 6,621,889 B1 | 9/2003 | Mostafavi |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,717,162 B1 | 4/2004 | Jongen |
| 6,769,806 B2 | 8/2004 | Moyers |
| 6,774,383 B2 | 8/2004 | Norimine et al. |
| 6,777,700 B2 | 8/2004 | Yanagisawa et al. |
| 6,800,866 B2 | 10/2004 | Amemiya et al. |
| 6,803,591 B2 | 10/2004 | Muramatsu et al. |
| 6,814,694 B1 * | 11/2004 | Pedroni ........................ 600/1 |
| 6,891,177 B1 | 5/2005 | Kraft et al. |
| 6,914,396 B1 | 7/2005 | Symons et al. |
| 7,014,361 B1 | 3/2006 | Ein-Gal |
| 7,026,636 B2 | 4/2006 | Yanagisawa et al. |
| 7,173,385 B2 | 2/2007 | Caporaso et al. |
| 7,208,748 B2 | 4/2007 | Sliski et al. |
| 7,348,579 B2 | 3/2008 | Pedroni |
| 7,402,963 B2 | 7/2008 | Sliski |
| 7,466,085 B2 | 12/2008 | Nutt |
| 7,476,883 B2 | 1/2009 | Nutt |
| 2003/0048080 A1 | 3/2003 | Amemiya et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |

| | | | |
|---|---|---|---|
| 2004/0232356 A1 | 11/2004 | Norimine et al. | |
| 2004/0240626 A1 | 12/2004 | Moyers | |
| 2005/0089141 A1 | 4/2005 | Brown | |
| 2005/0161618 A1 | 7/2005 | Eros | |
| 2005/0184686 A1 | 8/2005 | Caporaso et al. | |
| 2005/0228255 A1 | 10/2005 | Saracen et al. | |
| 2005/0234327 A1 | 10/2005 | Saracen et al. | |
| 2005/0247890 A1 | 11/2005 | Norimine et al. | |
| 2006/0126792 A1 | 6/2006 | Li | |
| 2006/0284562 A1 | 12/2006 | Hruby et al. | |
| 2007/0001128 A1 | 1/2007 | Sliski et al. | |
| 2007/0013273 A1 | 1/2007 | Albert et al. | |
| 2007/0014654 A1 | 1/2007 | Haverfield et al. | |
| 2007/0023699 A1* | 2/2007 | Yamashita et al. | 250/492.21 |
| 2007/0092812 A1 | 4/2007 | Caporaso et al. | |
| 2007/0145916 A1 | 6/2007 | Caporaso et al. | |
| 2007/0171015 A1* | 7/2007 | Antaya | 335/216 |
| 2007/0181519 A1* | 8/2007 | Khoshnevis | 212/180 |
| 2008/0093567 A1 | 4/2008 | Gall | |
| 2008/0218102 A1 | 9/2008 | Sliski | |
| 2009/0096179 A1 | 4/2009 | Stark et al. | |
| 2009/0140671 A1 | 6/2009 | O'Neal, III et al. | |
| 2009/0140672 A1 | 6/2009 | Gall et al. | |
| 2009/0200483 A1 | 8/2009 | Gall et al. | |

FOREIGN PATENT DOCUMENTS

| | | |
|---|---|---|
| DE | 31 48 100 | 6/1983 |
| DE | 3530446 | 8/1984 |
| DE | 41 01 094 C1 | 5/1992 |
| DE | 4411171 | 10/1995 |
| EP | 0194728 | 9/1986 |
| EP | 0 277 521 | 8/1988 |
| EP | 0208163 B1 | 1/1989 |
| EP | 0222786 | 7/1990 |
| EP | 0221987 | 1/1991 |
| EP | 0499253 | 8/1992 |
| EP | 0 306 966 | 4/1995 |
| EP | 0 388 123 | 5/1995 |
| EP | 0 465 597 | 5/1997 |
| EP | 0 864 337 | 9/1998 |
| EP | 0 776 595 | 12/1998 |
| EP | 1 069 809 | 1/2001 |
| EP | 1 153 398 A1 | 4/2001 |
| EP | 1 294 445 | 3/2003 |
| EP | 1 348 465 | 10/2003 |
| EP | 1 358 908 | 11/2003 |
| EP | 1 371 390 | 12/2003 |
| EP | 1 402 923 | 3/2004 |
| EP | 0 911 064 | 6/2004 |
| EP | 1 430 932 | 6/2004 |
| EP | 1430932 | 6/2004 |
| EP | 1 454 653 | 9/2004 |
| EP | 1 454 654 | 9/2004 |
| EP | 1 454 655 A2 | 9/2004 |
| EP | 1 454 656 | 9/2004 |
| EP | 1 454 657 | 9/2004 |
| EP | 1 477 206 | 11/2004 |
| EP | 1 605 742 A1 | 12/2005 |
| EP | 1738798 | 1/2007 |
| EP | 1826778 | 8/2007 |
| EP | 1949404 | 7/2008 |
| FR | 2 560 421 | 8/1985 |
| FR | 2911843 | 8/2008 |
| GB | 957342 | 5/1964 |
| GB | 2015821 A | 9/1979 |
| GB | 2 361 523 | 10/2001 |
| JP | 43-23267 | 10/1968 |
| JP | 61-80800 | 4/1986 |
| JP | 62-150804 | 7/1987 |
| JP | 62-186500 | 8/1987 |
| JP | 63-149344 | 6/1988 |
| JP | 63-218200 | 9/1988 |
| JP | 63-226899 | 9/1988 |
| JP | 1-276797 | 11/1989 |
| JP | 4-94198 | 3/1992 |
| JP | 04-128717 | 4/1992 |
| JP | 04-129768 | 4/1992 |
| JP | 04-273409 | 9/1992 |
| JP | 04-337300 | 11/1992 |
| JP | 05-341352 | 12/1993 |
| JP | 06233831 | 8/1994 |
| JP | 06233831 A | 8/1994 |
| JP | 06-036893 | 10/1994 |
| JP | 2007-260939 A | 10/1995 |
| JP | 07260939 | 10/1995 |
| JP | 08-173890 | 7/1996 |
| JP | 08-264298 | 10/1996 |
| JP | 09-162585 | 6/1997 |
| JP | 10-071213 | 3/1998 |
| JP | 11-47287 | 2/1999 |
| JP | 11-102800 | 4/1999 |
| JP | 11-243295 | 9/1999 |
| JP | 2000-294399 | 10/2000 |
| JP | 2001-6900 | 1/2001 |
| JP | 2001-129103 | 5/2001 |
| JP | 2002-164686 | 6/2002 |
| JP | 2009-515671 | 4/2009 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| WO | WO 86/07229 | 12/1986 |
| WO | WO90/012413 | 10/1990 |
| WO | WO 92/03028 | 2/1992 |
| WO | WO 93/02536 | 2/1993 |
| WO | WO 98/17342 | 4/1998 |
| WO | WO99/39385 | 8/1999 |
| WO | WO 00/40064 | 7/2000 |
| WO | WO 00/49624 | 8/2000 |
| WO | WO 01/26569 | 4/2001 |
| WO | WO 02/07817 | 1/2002 |
| WO | WO 03/039212 | 5/2003 |
| WO | WO 03/092812 | 11/2003 |
| WO | WO 2004/026401 | 4/2004 |
| WO | WO 2004/101070 | 11/2004 |
| WO | WO2007/061937 | 5/2007 |
| WO | WO 2007/061937 | 5/2007 |
| WO | WO2007/084701 | 7/2007 |
| WO | WO2007/130164 | 11/2007 |
| WO | WO2007/145906 | 12/2007 |
| WO | WO2008/030911 | 3/2008 |
| WO | WO 2009/048745 | 4/2009 |
| WO | WO2009-070173 | 6/2009 |
| WO | WO2009-070588 | 6/2009 |
| WO | WO2009-073480 | 6/2009 |
| WO | WO 2009/048745 | 11/2009 |

OTHER PUBLICATIONS

PCT International Search Report, PCT/US06/44853, Oct. 5, 2007.

International Search Report mailed Oct. 5, 2007 in corresponding PCT application No. PCT/US2006/44853 (12 pages).

Adachi, T., et. al. "A 150MeV FFAG Synchrotron with "Return-Yoke Free" Magent" *Proceedings of the 2001 Particle Accelerator Conference*, Chicago (2001).

Ageyev, A. I., et. al. "The IHEP Accelerating and Storage Complex (UNK) Status Report" *11th International Conference on High-Energy Accelerators*, pp. 60-70 (Jul. 7-11, 1980).

Agosteo, S., et. al. "Maze Design of a gantry room for proton therapy" *Nuclear Instruments & Methods in Physics Research*, Section A, 382, pp. 573-582 (1996).

Allardyce, B. W., et al., "Performance and Prospects of the Reconstructed CERN 600 MeV Synchrocyclotron" IEEE Transactions on Nuclear Science USA ns-24:(3), pp. 1631-1633 (Jun. 1977).

Alexeev, V. P., et. al. "R4 Design of Superconducting Magents for Proton Synchrotrons" *Proceedings of the Fifth International Cryogenic Engineering Conference*, pp. 531-533 (1974).

Amaldi, U. "Overview of the world landscape of Hadrontherapy and the projects of the TERA foundation" *Physica Medica, an International journal Devoted to the Applications of Physics to Medicine and Biology*, vol. XIV, Supplement 1 (Jul. 1998), *6th Workshop on Heavy Charged Particles in Biology and Medicine*, Instituto Scientific Europeo (ISE), Baveno, pp. 76-85 (Sep. 29-Oct. 1, 1997).

Amaldi, U., et. al. "The Italian project for a hadrontherapy centre" *Nuclear Instruments and Methods in Physics Research A*, 360, pp. 297-301 (1995).

Anferov, V., et. al. "The Indiana University Midwest Proton Radiation Institute" *Proceedings of the 2001 Particle Accelerator Conference*, Chicago, pp. 645-647 (2001).

Anferov, V., et. al. "Status of the Midwest Proton Radiotherapy Institute", *Proceedings of the 2003 Particle Accelerator Conference*, pp. 699-701 (2003).

Appun, J. "Various problems of magnet fabrication for high-energy accelerators" *Journal for All Engineers Interested in the Nuclear Field*, pp. 10-16 (1967) [Lang.: German], English bibliographic information (http://www.osti.gov/energycitations/product.biblio.jsp?osti_id=4442292).

Arduini, G., et. al. "Physical specifications of clinical proton beams from a synchrotron" *Med. Phys.* 23 (6), pp. 939-951 (Jun. 1996).

Beckman, W., et. al. "Preliminary design of a reduced cost proton therapy facility using a compact, high field isochronous cyclotron" *Nuclear Instruments and Methods in Physics Reasearch B56/57*, pp. 1201-1204 (1991).

Benedikt, M. and Carli, C. "Matching to Gantries for Medical Synchrotrons" *IEEE Proceedings of the 1997 Particle Accelerator Conference*, pp. 1379-1381 (1997).

Bieth, C., et. al. "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, pp. 669-672 (Jun. 14-19, 1998).

Blackmore, E. W., et. al. "Operation of the Triumf Proton Therapy Facility" *IEEE Proceedings of the 1997 Particle Accelerator Conferenc*, vol. 3, pp. 3831-3833 (May 12-16, 1997).

Bloch, C. "The Midwest Proton Therapy Center" *Application of Accelerators in Research and Industry, Proceedings of the Fourteenth Int'l. Conf.*, Part Two, pp. 1253-1255 (Nov. 1996).

Blosser, H. G. "Compact Superconducting Synchrocyclotron Systems for Proton Therapy" *Nuclear Instruments & Methods in Physics Research*, Section B40-41, Part II, pp. 1326-1330 (Apr. 1989).

Blosser, H. "Applications of Superconducting Cyclotrons" *Twelfth International Conference on Cyclotrons and Their Applications*, pp. 137-144 (May 8-12, 1989).

Blosser, H., et. al. "Medical Accelerator Projects at Michigan State Univ." *IEEE Proceedings of the 1989 Particle Accelerator Conference*, vol. 2, pp. 742-746 (Mar. 20-23, 1989).

Blosser, H., et. al. "A Compact Superconducting Cyclotron for the Production of High Intensity Protons" *Proceedings of the 1997 Particle Accelerator Conference*, vol. 1, pp. 1054-1056 (May 12-16, 1997).

Blosser, H. G. "Synchrocyclotron Improvement Programs" *IEEE Transactions on Nuclear Science USA*, vol. 16, No. 3, Part I, pp. 405-414 (Jun. 1969).

Botha, A. H., et. al. "A New Multidisciplinary Separated-Sector Cyclotron Facility" IEEE Transactions on Nuclear Science, vol. NS-24, No. 3, pp. 1118-1120 (1977).

Chu, et. al. "Instrumentation for Treatment of Cancer Using Proton and Light-ion Beams" Review of Scientific Instruments, 64 (8), pp. 2055-2122 (Aug. 1993).

Cole, et. al. "Design and Application of a Proton Therapy Accelerator", Fermi National Accelerator Laboratory, IEEE, 1985.

Conradie, et. al. "Proposed New Facilities for Proton Therapy at iThemba Labs" Proceedings of EPAC, pp. 560-562 (2002).

Coupland, . "High-field (5 T) pulsed superconducting dipole magnet" Proceedings of the Institution of Electrical Engineers, vol. 121, No. 7, pp. 771-778 (Jul. 1974).

Coutrakon, G et al. "Proton Synchrotrons for Cancer Therapy" Application of Accelerators in Research and Industry—Sixteenth International Conf., American Institute of Physics, vol. 576, pp. 861-864 (Nov. 1-5, 2000).

Coutrakon, et. al. "A prototype beam delivery system for the proton medical accelerator at Loma Linda" Medical Physics, vol. 18(6), pp. 1093-1099 (Nov./Dec. 1991).

Dahl, P., "Superconducting Magnet System" American Institute of Physics, AIP Conference Proceedings, vol. 2, pp. 1329-1376 (1987-1988).

Dugan, G. et al. "Tevatron Status" IEEE, Particle Accelerator Conference, Accelerator Science & Technology (1989), pp. 426-430.

Eickhoff, et al. "The Proposed Accelerator Facility for Light Ion Cancer Therapy in Heidelberg" Proceedings of the 1999 Particle Accelerator Conference, New York, pp. 2513-2515 (1999).

Enchevich, B. et al., "Minimizing Phase Losses in the 680 MeV Synchrocyclotron by Correcting the Accelerating Voltage Amplitude," *Atomnaya Energiya* 26:(3), pp. 315-316 (1969).

Endo, K., et. al., "Compact Proton and Carbon Ion Synchrotrons for Radiation Therapy" Proceedings of EPAC 2002, Paris France, pp. 2733-2735 (2002).

Flanz, et. al. "Treating Patients with the NPTC Accelerator Based Proton Treatment Facility" Proceedings of the 2003 Particle Accelerator Conference (2003), pp. 690-693.

Flood, W. S. and Frazier, P. E. "The Wide-Band Driven RF System for the Berkeley 88-Inch Cyclotron" American Institute of Physics, Conference Proceedings., No. 9, 459-466 (1972).

Foster, G. W. and Kashikhin, V. S. "Superconducting Superferric Dipole Magent with Cold Iron Core for the VLHC" IEEE Transactions on Applied Superconductivity, vol. 12, No. 1, pp. 111-115 (Mar. 2002).

Friesel, D. L. et al. "Design and Construction Progress on the IUCF Midwest Proton Radiation Institute" Proceedings of EPAC 2002, pp. 2736-2738 (2002).

Fukumoto, et. al., "A Proton Therapy Facility Plan" Cyclotrons and their Applications, Proceedings of the 13th International Conference, Vancouver, Canada, pp. 258-261 (Jul. 6-10, 1992).

Gordon, et. al. "Design Study for a Compact 200 MeV Cyclotron" AIP Conference Proceedings Sixth International Cyclotron Conference, No. 9, pp. 78-86 (1972).

Gordon, M. M., "Extraction Studies for a 250 MeV Superconducting Synchrocyclotron", Proceedings of the 1987 IEEE Particle Accelerator Conference: Accelerator Engineering and Technology, pp. 1255-1257 (1987).

Graffman, et. al. "Proton radiotherapy with the Uppsala cyclotron. Experience and plans" Strahlentherapie, 161, No. 12, pp. 764-770 (1985).

Graffman, et. al. "Design Studies for a 200 MeV Proton Clinic for Radiotherapy" AIP Conference Proceedings: Cyclotrons—1972, No. 9, pp. 603-615 (1972).

Heinz, . "Superconducting Pulsed Magnetic Systems for High-Energy Synchrotrons" *Proceedings of the Fourth International Cryogenic Engineering Conference*, pp. 55-63. (May 24-26, 1972).

Hentschel, R., et. al., "Plans for the German National Neutron Therapy Centre with a Hospital-Based 70 MeV Proton Cyclotron at University Hospital Essen/Germany" *Cyclotrons and their Applications, Proceedings of the Fifteenth International Conference on Cyclotrons and their Applications*, Caen, Franco, pp. 21-23 (Jun. 14-19, 1998).

Hepburn, et. al. "Superconducting Cyclotron Neutron Source for Therapy" *International Journal of Radiation Oncology Biology Physics*, vol. 3 complete, pp. 387-391 (1977).

Hirabayashi, H. "Development of Superconducting Magnets for Beam Lines and Accelerator at KEK" *IEEE Transaction on Magnetics*, vol. Mag-17, No. 1, pp. 728-731 (Jan. 1981).

"Indiana's mega-million proton therapy cancer center welcomes its first patients" [online] Press release, Health & Medicine Week, 2004, retrieved from NewsRx.com, Mar. 1, 2004, pp. 119-120.

Ishibashi, K. and McInturff, A. "Winding Design Study of Superconducting 10 T Dipoles for a Synchrotron" *IEEE Transactions on Magnetics*, vol. MAG-19, No. 3, pp. 1364-1367 (May 1983).

Jahnke, A., et. al. "First Superconducting Prototype Magnets for a Compact Synchrotron Radiation Source in Operation" *IEEE Transactions on Magnetics*, vol. 24, No. 2 (Mar. 1988), pp. 1230-1232.

Jones, D.T.L. "Progress with the 200 MeV Cyclotron Facility at the National Accelerator Centre" *Commission of the European Communities Radiation Protection Proceedings, Fifth Symposium on Neutron Dosimetry*, vol. II, pp. 989-998 (Sep. 17-21, 1984).

Jones, D. T. L. "Present Status and Future Trends of Heavy Particle Radiotherapy" *Cyclotrons and their Applications 1998, Proceedings of the Fifteenth International Conference on Cyclotrons and their Applications*, pp. 13-20 (Jun. 14-19, 1998).

Jones, . and Dershem . "Synchrotron Radiation from Proton in a 20 TEV, 10 TESLA Superconducting Super Collider" *Proceedings of the 12th International Conference on High-Energy Accelerators*, pp. 138-140 (Aug. 11-16, 1983).

Jones, D. T. L. and Mills, S. J. "The South African National Accelerator Centre: Particle Therapy and Isotope Production Programmes" *Radiation Physics and Chemistry*, vol. 51, Nos. 4-6, pp. 571-578 (Apr.-Jun. 1998).

Jones, D. T. L., et. al. "Status Report of the NAC Particle Therapy Programme" *Stralentherapie und Onkologie*, vol. 175, Suppl. II, pp. 30-32 (Jun. 1999).

Jongen, Y., et. al. "Progress report on the IBA-SHI small cyclotron for cancer therapy" *Nuclear Instruments and Methods in Physics Research*, Section B, vol. 79, issue 1-4, pp. 885-889 (1993).

Jongen, Y., et. al. "The proton therapy system for MGH's NPTC: equipment description and progress report" *Bulletin du Cancer/Radiotherapie, Proceedings of the meeting of the European Heavy Particle Therapy Group*, vol. 83, Suppl. 1, pp. 219-222 (1996).

Jongen, Y., et. al. "Development of a Low-cost Compact Cyclotron System for Proton Therapy" *National Institute of Radiol. Sci.*, No. 81, pp. 189-200 (1991).

Jongen, Y. et. al. "The proton therapy system for the NPTC: equipment description and progress report" *Nuclear Instruments and methods in Physics Research*, Section B, vol. 113, No. 1, pp. 522-525 (1996).

Kats, M.M. and Druzhinin, B.L. "Comparison of Methods for Irradiation Prone Patients" *Atomic Energy*, vol. 94, No. 2, pp. 120-123 (Feb. 2003).

Kats, M. M. and Onosovskii, K. K. "A Planar Magnetooptical System for the Irradiation of a Lying Patient with a Proton Beam from Various Directions" *Instruments and Experimental Techniques*, vol. 39, No. 1, pp. 127-131 (1996).

Kats, M. M. and Onosovskii, K. K. "A Simple, Compact, Flat System for the Irradiation of a Lying Patient with a Proton Beam from Different Directions" *Instruments and Experimental Techniques*, vol. 39, No. 1, pp. 132-134 (1996).

Koehler, A.M., et al., "Range Modulators for Protons and Heavy Ions," *Nuclear Instruments and Methods*, vol. 131, pp. 437-440 (1975).

Khoroshkov, V. S., et. al. "Moscow Hospital-Based Proton Therapy Facility Design" *Am. Journal Clinical Oncology: CCT*, vol. 17, No. 2, pp. 109-114 (Apr. 1994).

Kim, J. and Yun, C. "A Light-Ion Superconducting Cyclotron System for Multi-Disciplinary Users" *Journal of the Korean Physical Society*, vol. 43, No. 3, pp. 325-331 (Sep. 2003).

Kishida, N. and Yano, Y. "Beam Transport System for the RIKEN SSC (II)" *Scientific Papers of the Institute of Physical and Chemical Research*, vol. 75, No. 4, pp. 214-235 (Dec. 1981).

Koto, M. and Tsujii, H. "Future of Particle Therapy" *Japanese Journal of Cancer Clinics*, vol. 47, No. 1, pp. 95-98 (2001) [Lang.: Japanese], English abstract (http://sciencelinks.jp/j-east/article/200206/000020020601A0511453.php).

Larsson, B. "Biomedical Program for the Converted 200-MeV Synchrocyclotron at the Gustaf Werner Institute" *Radiation Research*, 104, pp. S310-S318 (1985).

Lecroy, W., et al., "Viewing Probe for High Voltage Pulses", *Review of Scientific Instruments USA* 31(12), p. 1354 (Dec. 1960).

Livingston, M. S., et. al. "A Capillary Ion Source for the Cyclotron" *Review Science Instruments*, vol. 10:63 (Feb. 1939).

Mandrillon, P. "High Energy Medical Accelerators" *EPAC 90, 2nd European Particle Accelerator Conference*, vol. 2, (Jun. 12-16, 1990), pp. 54-58.

Martin, P. "Operational Experience with Superconducting Synchrotron Magnets" *Proceedings of the 1987 IEEE Particle Accelerator Conference*, vol. 3 of 3, pp. 1379-1382 (Mar. 16-19, 1987).

Meot, F., et. al. "ETOILE Hadrontherapy Project, Review of Design Studies" *Proceedings of EPAC 2002*, pp. 2745-2747 (2002).

Miyamoto, S., et. al. "Development of the Proton Therapy System" *The Hitachi Hyoron*, vol. 79, 10, pp. 775-779 (1997) [Lang: Japanese], English abstract (http://www.hitachi.com/rev/1998/revfeb98/rev4706.htm).

Montelius, A., et. al. "The Narrow Proton Beam Therapy Unit at the Svedberg Laboratory in Uppsala" *ACTA Oncologica*, vol. 30, pp. 739-745 (1991).

Nicholson, J. "Applications of Proton Beam Therapy" *Journal of the American Society of Radiologic Technologists*, vol. 67, No. 5, pp. 439-441 (May/Jun. 1996).

"Proton Therapy Center Nearing Completion" *R&D Magazine*, vol. 41, No. 9, S-47 (Aug. 1999).

Norimine, T., et. al. "A Design of a Rotating Gantry with Easy Steering for Proton Therapy" *Proceedings of EPAC 2002*, pp. 2751-2753 (2002).

Okumura, T., et. al. "Overview and Future Prospect of Proton Radiotherapy" *Japanese Journal of Cancer Clinics*, vol. 43, No. 2, pp. 209-214 (1997) [Lang.: Japanese].

Okumura, T., et. al. "Proton Radiotherapy" *Japanese Journal of Cancer and Chemotherapy*, 10. 20, No. 14, pp. 2149-2155 (1993) [Lang.: Japanese].

Palmer, R. and Tollestrup, A. V. "Superconducting Magnet Technology for Accelerators" *Annual Review of Nuclear and Particle Science*, vol. 34, pp. 247-284 (1984).

Pavlovic, M. "Beam-optics study of the gantry beam delivery system for light-ion cancer therapy" *Nuclear Instruments and Methods in Physics Research*, Section A, vol. 399, No. 2, pp. 439-454(16) (Nov. 1997).

Pedroni, E. "Accelerators for Charged Particle Therapy: Performance Criteria from the User Point of View" *Cyclotrons and their Applications, Proceedings of the 13th International Conference*, pp. 226-233 (Jul. 6-10, 1992).

Pedroni, E. "Latest Developments in Proton Therapy" *Proceedings of EPAC 2000*, pp. 240-244 (2000).

Pedroni, E., et. al. "The 200-MeV proton therapy project at the Paul Scherrer Institute: Conceptual design and practical realization" *Medical Physics*, vol. 22, No. 1, pp. 37-53 (Jan. 1995).

Pedroni, E., et. al. "A Novel Gantry for Proton Therapy at the Paul Scherrer Institute" *Cycloctrons and Their Applications 2001: Sixteenth International Conference. AIP Conference Proceedings*, vol. 600, pp. 13-17 (2001).

Pedroni, E. and Enge, H. "Beam optics design of compact gantry for proton therapy" *Medical & Biological Engineering & Computing*, vol. 33, No. 3, pp. 271-277 (May 1995).

Pedroni, E. and Jermann, M. "SGSMP: Bulletin 3/2002 Proscan Project, Progress Report on the PROSCAN Project of PSI" [online] retrieved from www.sgsmp.ch/protA23.htm, (5 pages) Mar. 2002.

Potts, R., et. al. "MPWP6—Therapy III: Treatment Aids and Techniques" *Medical Physics*, vol. 15, No. 5, p. 798 (Sep./Oct. 1988).

Prieels, D., et. al. "The IBA State-of-the-Art Proton Therapy System, Performances and Recent Results" *Application of Accelerators in Research and industry—Sixteenth Int'l. Conf., American Institute of Physics*, vol. 576, pp. 857-860 (Nov. 1-5, 2000).

Rabin, M. S. Z., et. al. "Compact Designs for Comprehensive Proton Beam Clinical Facilities" *Nuclear Instruments & Methods in Physics Research*, Section B, vol. 40-41, Part II, pp. 1335-1339 (Apr. 1989).

Rifuggiato, D., et. al. "Status Report of the LNS Superconducting Cyclotron" *Nukleonika*, vol. 48, pp. S131-S134 (Supplement 2, 2003).

Rode, C. H. "Tevatron Cryogenic System" *Proceedings of the 12th International Conference on High-energy Accelerators, Fermilab*, pp. 529-535 (Aug. 11-16, 1983).

Schillo, M., et. al. "Compact Superconducting 250 MeV Proton Cyclotron for the PSI Proscan Proton Therapy Project" *Cyclotrons and Their Applications 2001, Sixteenth International Conference*, pp. 37-39 (2001).

Schreuder, H.W. "Recent Developments in Superconducting Cyclotrons" *Proceedings of the 1995 Particle Accelerator Conference*, vol. 1, pp. 317-321 (May 1-5, 1995).

Schreuder, A. N., et. al. "The Non-orthogonal Fixed Beam Arrangement for the Second Proton Therapy Facility at the National Accelerator Centre" *Application of Accelerators in Research and Industry, American Institute of Physics, Proceedings of the Fifteenth International Conference*, Part Two, pp. 963-966 (Nov. 1998).

Schubert, J. R. "Extending the Feasibility Boundary of the Isochronous Cyclotron" Dissertation submitted to Michigan State University, 1997, Abstract http://adsabs.harvard.edu/abs/1998PhDT.......147S.

Schubert, J. and Blosser, H. "Conceptual Design of a High Field Ultra-Compact Cyclotron for Nuclear Physics Research" *Proceedings of the 1997 Particle Accelerator Conference*, vol. 1, pp. 1060-1062 (May 12-16, 1997).

Shelaev, I. A., et. al. "Design Features of a Model Superconducting Synchrotron of JINR" *Proceedings of the 12th International Conference on High-energy Accelerators*, pp. 416-418 (Aug. 11-16, 1983).

Shintomi, T., et. al. "Technology and Materials for the Superconducting Super Collider (SSC) Project" [Lang.: Japanese], The Iron and Steel Institute of Japan 00211575, vol. 78, No. 8 (Aug. 1, 1992), pp. 1305-1313, http://ci.nii.ac.jp/naid/110001493249/en/ , 1992.

Sisterson, J. M. "World Wide Proton Therapy Experience in 1997" *The American Institute of Physics, Applications of Accelerators in Research and Industry, Proceedings of the Fifteenth International Conference*, Part Two, pp. 959-962 (Nov. 1998).

Sisterson, J. M. "Clinical Use of Proton and Ion Beams From a World-Wide Perspective" *Nuclear Instruments and Methods in Physics Research*, Section B, vols. 40-41, pp. 1350-1353 (1989).

Slater, J. M., et. al. "Development of a Hospital-Based Proton Beam Treatment Center" *International Journal of Radiation Oncology Biology Physics*, vol. 14, No. 4, pp. 761-775 (Apr. 1988).

Slater, J. M., et. al. "Developing a Clinical Proton Accelerator Facility: Consortium-Assisted Technology Transfer" *Conference Record of the 1991 IEEE Particle Accelerator Conference: Accelerator Science and Technology*, vol. 1, pp. 532-536 (May 6-9, 1991).

Smith, A., et. al. "The Northeast Proton Therapy Center at Massachusetts General Hospital" *Journal of Brachytherapy International*, pp. 137-139 (Jan. 1997).

Snyder, S. L. and Marti, F. "Central region design studies for a proposed 250 MeV proton cyclotron" *Nuclear Instruments and Methods in Physics Research*, Section A, vol. 355, pp. 618-623 ((1995)).

Soga, F. "Progress of Particle Therapy in Japan" *Application of Accelerators in Research and Industry, American Institute of Physics, Sixteenth International Conference*, pp. 869-872 (Nov. 2000).

Spiller, P., et. al. "The GSI Synchrotron Facility Proposal for Acceleration of High Intensity Ion and Proton Beams" *Proceedings of the 2003 Particle Accelerator Conference*, vol. 1, pp. 589-591 (May 12-16, 2003).

Takada, Y. "Conceptual Design of a Proton Rotating Gantry for Cancer Therapy" *Japanese Journal of Medical Physics*, vol. 15, No. 4, pp. 270-284 (1995).

Teng, L. C. "The Fermilab Tevatron" *Coral Gables 1981, Proceedings, Gauge Theories, Massive Neutrinos, and Proton Decay*, pp. 43-62 (1981).

Tom, J. L. "The Use of Compact Cyclotrons for Producing Fast Neutrons for Therapy in a Rotatable Isocentric Gantry" *IEEE Transaction on Nuclear Science*, vol. 26, No. 2, pp. 2294-2298 (Apr. 1979).

Trinks, U., et. al. "The Tritron: A Superconducting Separated-Orbit Cyclotron" *Nuclear Instruments and Methods in Physics Research*, Section A, vol. 244, pp. 273-282 (1986).

Tsuji, H. "The Future and Progress of Proton Beam Radiotherapy" *Journal of Japanese Society for Therapeutic Radiology and Oncology*, vol. 6, No. 2, pp. 63-76 (1994).

Umegaki, K., et. al. "Development of an Advanced Proton Beam Therapy System for Cancer Treatment" *Hitachi Hyoron*, vol. 85, No. 9, pp. 605-608 (2003) [Lang.: Japanese], English abstract, http://www.hitachi.com/ICSFiles/afieldfile/2004/06/01/r2003_04_104.pdf or http://www.hitachi.com/rev/archive/2003/2005649_12606.html (full text) [Hitachi, vol. 52, No. 4 Dec. 2003].

Umezawa, M., et. al. "Beam Commissioning of the new Proton Therapy System for University of Tsukuba" *Proceedings of the 2001 Particle Accelerator Conference*, vol. 1, pp. 648-650 (Jun. 18-22, 2001).

van Steenbergen, A. "The CMS, a Cold Magnet Synchrotron to Upgrade the Proton Energy Range of the BNL Facility" *IEEE Transactions on Nuclear Science*, vol. 18, Issue 3, pp. 694-698 (Jun. 1971).

van Steenbergen, A. "Superconducting Synchroton Development at BNL" *Proceedings of the 8th International Conference on High-Energy Accelerators CERN 1971*, pp. 196-198 (1971).

Vandeplassche, D., et. al. "235 MeV Cyclotron for MGH's Northeast Proton Therapy Center (NPTC): Present Status" EPAC 96, *Fifth European Partical Accelerator Conference*, vol. 3, pp. 2650-2652 (Jun. 10-14, 1996).

Vrenken, H., et. al. "A Design of a Compact Gantry for Proton Therapy with 2D-Scanning" *Nuclear Instruments and Methods in Physics Research*, Section A, vol. 426, No. 2, pp. 618-624 (1999).

Yudelev, M., et. al. "Hospital Based Superconducting Cyclotron for Neutron Therapy: Medical Physics Perspective" *Cyclotrons and their applications 2001, 16th International Conference. American Institute of Physics Conference Proceedings*, vol. 600, pp. 40-43 (May 13-17, 2001) http://www.osti.gov/energycitations/product.biblio.jsp?osti_id=20468164 http://adsabs.harvard.edu/abs/2001AIPC..600...40Y http://scitation.aip.org/getabs/servlet/GetabsServlet?prog=normal& id=APCPCS000600000001000040000001&idtype=cvips& gifs=yes.

"The K100 Neutron-therapy Cyclotron," National Superconducting Cyclotron Laboratory at Michigan State University (NSCL), retrieved from: http://www.nscl.msu.edu/tech/accelerators/k100 , Feb. 2005.

"The K250 Proton therapy Cyclotron," National Superconducting Cyclotron Laboratory at Michigan State University (NSCL), retrieved from: http://www.nscl.msu.edu/tech/accelerators/k250.html , Feb. 2005.

"The K250 Proton-therapy Cyclotron Photo Illustration," National Superconducting Cyclotron Laboratory at Michigan State University (NSCL), retrieved from: http://www.nscl.msu.edu/media/image/experimental-equipment-technology/250.html , Feb. 2005.

Literature Keyword Search, Jan. 24, 2005 (96 pages).

Patent Assignee and Keyword Searches for Synchrocyclotron, Jan. 25, 2005 (77 pages).

Literature Search, Jan. 26, 2005 (36 pages).

Revised Patent Keyword Search, Jan. 25, 2005 (88 pages).

Literature Search by Company Name/Component Source, Jan. 24, 2005 (111 pages).

Worldwide Patent Keyword Search, Jan. 24, 2005 (94 pages).

Dialog Search, Jan. 31, 2005 (17 pages).

Literature Search and Keyword Search for Synchrocyclotron, Jan. 25, 2005 (68 pages).

Outstanding from Search Reports, "Accelerator of Polarized Portons at Fermilab," 20 pages, 2005.

RetroSearch "Bernard Gottschalk, Cyclotron, Beams, Compensated Upstream Modulator, Compensated Scatter," Jan. 21, 2005 (20 pages).

RetroSearch Gottschalk, Bernard, Harvard Cyclotron Wheel, Jan. 21, 2005 (20 pages).

RetroSearch "Loma Linda University, Beam Compensation Foil Wedge," Jan. 21, 2005 (15 pages).

RetroSearch "Loma Linda University Beam Compensation," Jan. 21, 2005 (60 pages).

RetroSearch "Berkeley 88-Inch Cyclotron 'RF' or 'Frequency Control'," Jan. 21, 2005 (36 pages).

RetroSearch "Cyclotron with 'RF' or 'Frequency Control'," Jan. 21, 2005 (49 pages).

RetroSearch "Berkeley 88-Inch Cyclotron," Jan. 24, 2005 (170 pages).

"Patent Assignee Search Paul Scherrer Institute," Library Services at Fish & Richardson P.C., Mar. 20, 2007 (40 pages).

"Patent Prior Art Search for 'Proton Therapy System'," Library Services at Fish & Richardson P.C., Mar. 20, 2007 (46 pages).
U.S. Appl. No. 60/738,404, filed Nov. 18, 2005, including application as filed, transaction history from PAIR (PTO website).
U.S. Appl. No. 11/948,359, filed Nov. 30, 2007, including application as filed (including pending claims), transaction history from PAIR (PTO website).
PCT application No. PCT/US2006/44853, filed on Nov. 17, 2006, with Publication No. WO/2007/061937, including application as filed, transaction history from PAIR (PTO website).
U.S. Appl. No. 10/949,734, filed Sep. 24, 2004, Patent No. 7,208,748, issued on Apr. 24, 2007, including application as filed, transaction history from PAIR (PTO website), and allowed claims.
U.S. Appl. No. 11/724,055, filed Mar. 14, 2007, including application as filed (including pending claims), transaction history from PAIR (PTO website).
U.S. Appl. No. 11/371,622, filed Mar. 9, 2006, including application as filed, transaction history from PAIR (PTO website), and pending claims.
U.S. Appl. No. 60/590,088, filed Jul. 21, 2004, including application as filed, transaction history from PAIR (PTO website).
U.S. Appl. No. 11/187,633, filed Jul. 21, 2005, including application as filed, transaction history from PAIR (PTO website), and pending claims.
PCT application No. PCT/US2005/25942 filed on Jul. 21, 2005, with Publication No. WO/2006/012452, including application as filed, transaction history from PAIR (PTO website).
U.S. Appl. No. 11/463,403, filed Aug. 9, 20006, including application as filed (including pending claims), transaction history from PAIR (PTO website).
U.S. Appl. No. 11/517,490, filed Sep. 7, 2006, including application as filed (including pending claims), transaction history from PAIR (PTO website).
U.S. Appl. No. 11/624,769, filed Jan. 19, 2007, including application as filed (including pending claims), transaction history from PAIR (PTO website).
PCT application No. PCT/US2007/01506 filed on Jan. 19, 2007, with Publication No. WO/2007/084701, including application as filed, transaction history from PAIR (PTO website).
PCT application No. PCT/US2007/01628 filed on Jan. 19, 2007, with Publication No. WO/2007/130164, including application as filed, transaction history from PAIR (PTO website).
PCT application No. PCT/US2007/77693 filed on Sep. 6, 2007 with Publication No. WO/2007/77693, including application as filed, transaction history from PAIR (PTO website).
International Search Report dated Aug. 26, 2008 in PCT application No. PCT/US2007/086109 (6 pages).
Written Opinion dated Aug. 26, 2008 in PCT application No. PCT/US2007/086109 (6 pages).
"CPAC Highlights Its Proton Therapy Program at ESTRO Annual Meeting", TomoTherapy Incorporated, Sep. 18, 2008, Madison, Wisconsin, pp. 1-2.
"An Accelerated Collaboration Meets with Beaming Success", Lawrence Livermore National Laboratory, Apr. 12, 2006, Livermore, California, pp. 1-3.
UC Davis School of Medicine, "Unlikely Partners Turn Military Defense into Cancer Offense", Current Issue Summer 2008, Sacramento, California, pp. 1-2.
"LLNL, UC Davis Team Up to Fight Cancer", Lawrence Livermore National Laboratory, Apr. 28, 2006, SF-06-04-02, Livermore, California, pp. 1-4.
Hede, Karyn, "Research Groups Promoting Proton Therapy "Lite"", Journal of the National Cancer Institute, vol. 98, No. 23, Dec. 6, 2006, pp. 1682-1684.
European Patent Office communication for application No. 06838033.6, patent No. 1949404, mailed Aug. 5, 2009 (1 page).
Invitation to Pay Additional Fees and, where applicable, Protest Fees with partial search report for application No. PCT/US2008/077513 mailed Jul. 3, 2009 (62 pages).
Flanz, et al., "Operation of a Cyclotron Based Proton Therapy Facility", Massachusetts General Hospital, Boston, MA 02114, pp. 1-4.
Resmini, F., "Design Characteristics of the K=800 Superconducting Cyclotron at M.S.U.", Cyclotron Laboratory, Michigan State University, East Lansing, Michigan 48824, IEEE Transaction on Nuclear Science, vol. NS-26, No. 2, Apr. 1979 (8 pages).
International Search Report and Written Opinion mailed Oct. 1, 2009 in PCT application No. PCT/US2008/077513 (73 pages).
International Search Report and Written Opinion for PCT application No. PCT/US2008/084699 mailed Feb. 4, 2009 (11 pages).
International Search Report and Written Opinion for PCT application No. PCT/US2008/084695 mailed Jan. 26, 2009 (15 pages).
International Search Report and Written Opinion for PCT application No. PCT/US2007/001506 mailed Jul. 5, 2007, Publication No. WO2007/084701, Published Jul. 26, 2007 (14 pages).
International Preliminary Report on Patentability for PCT application No. PCT/US2007/001506 mailed Jul. 5, 2007 (15 pages).
International Search Report for PCT/US2007/001628 mailed Feb. 18, 2008 (4 pages).
Written Opinion for PCT/US2007/001628, mailed Feb. 18, 2008 (11 pages).
International Preliminary Report on Patentability for PCT/US2007/001628, mailed Apr. 22, 2008 (15 pages).
U.S. Appl. No. 11/870,961, filed on Oct. 11, 2007, including application as filed (including pending claims), transaction history from Pair (PTO website).
PCT application No. PCT/US2008/077513, filed on Sep. 24, 2008, including application as filed, transaction history from Pair (PTO website).
PCT application No. PCT/US2008/084695 filed on Nov. 25, 2008, including application as filed, transaction history from Pair (PTO website).
PCT application No. PCT/US2008/084699 filed on Nov. 25, 2008, including application as filed, transaction history from Pair (PTO website). U.S. Appl. No. 60/991,454, filed on Nov. 30, 2007, including application as filed, transaction history from Pair (PTO website).
U.S. Appl. No. 60/991,454, filed on Nov. 30, 2007, including application as filed, transaction history from PAIR (PTO website).
U.S. Appl. No. 12/275,103, filed on Nov. 20, 2008, including application as filed (including pending claims), transaction history from Pair (PTO website).
PCT application No. PCT/US2007/086109 filed on Nov. 30, 2007, including application as filed, transaction history from Pair (PTO website).
U.S. Appl. No. 60/850,565, filed on Oct. 10, 2006, including application as filed, transaction history from Pair (PTO website).
Abrosimov, N. K., et al. Proc. Academy Science, USSR 5, 84 (1985).
Abrosimov, N. K., et al, "1000MeV Proton Beam Therapy facility at Petersburg Nuclear Physics Institute Synchrocyclotron", Medical Radiology (Moscow) 32, 10 (1987) revised in Journal of Physics, Conference Series 41, pp. 424-432, Institute of Physics Publishing Limited, 2006.
"An Accelerated Collaboration Meets with Beaming Success", S&TR, Apr. 2006, http://www.llnl.gov/str/April06/Caporaso.html.
Bellomo, G., et al., "The Superconducting Cyclotron Program at Michigan State University" *Bulletin of the American Physical Society*, vol. 25, No. 7, pp. 767 (Sep. 1980).
Bigham, C.B. "Magnetic Trim Rods for Superconducting Cyclotrons," Nuclear Instruments and Methods (North-Holland Publishing Co.) 141 (1975), pp. 223-228.
Blosser, H., et al., "Advances in Superconducting Cyclotrons at Michigan State University", Proceedings of the 11th International Conference on Cyclotrons and their Applications, pp. 157-167 (Oct. 1986), Tokyo.
Blosser, H., "Application of Superconductivity in Cyclotron Construction", *Ninth International Conference on Cyclotrons and their Applications*, pp. 147-157 (Sep. 1981).
Blosser, H., et al., "Characteristics of a 400 (Q2/A) MeV Super-Conducting Heavy-Ion Cyclotron", Bulletin of the American Physical Society, p. 1026 (Oct. 1974).
Blosser, H.G., "Future Cyclotrons" AIP, *The Sixth International Cyclotron Conference*, pp. 16-32 (1972).
Blosser, H.G., "Medical Cyclotrons", *Physics Today*, Special Issue Physical Review Centenary, pp. 70-73 (Oct. 1993).
Blosser, H., et al, National Superconducting Cyclotron Laboratory, Michigan State University, Report MSUCL-760.

Blosser, H., et al., "Preliminary Design Study Exploring Building Features Required for a Proton Therapy Facility for the Ontario Cancer Institute", MSUCL-760a (Mar. 1991).
Blosser, H., Present and Future Superconducting Cyclotrons, *Bulletin of the American Physical Society*, vol. 32, No. 2, p. 171 (Feb. 1987), Particle Accelerator Conference, Washington, D.C. 1987.
Blosser, H.G., "Program on the Coupled Superconducting Cyclotron Project", *Bulletin of the American Physical Society*, vol. 26, No. 4, p. 558 (Apr. 1981).
Blosser, H., et al., "Problems and Accomplishments of Superconducting Cyclotrons", Proceedings of the 14th International Conference, Cyclotrons and Their Applications, pp. 674-684 (Oct. 1995).
Blosser, H., et al., "Superconducting Cyclotron for Medical Application", *IEEE Transactions on Magnetics*, vol. 25, No. 2, pp. 1746-1754 (Mar. 1989).
Blosser, H.G., et al., "Superconducting Cyclotrons", Seventh International Conference on Cyclotrons and their Applications, pp. 584-594 (Aug. 19-22, 1975).
Blosser, H.G., "Superconducting Cyclotrons at Michigan State University", Nuclear Instruments & Methods in Physics Research, vol. B 24/25, part II, pp. 752-756 (1987).
Blosser, H.G., "The Michigan State University Superconducting Cyclotron Program", Nuclear Science, vol. NS-26, No. 2, pp. 2040-2047 (Apr. 1979).
Chichili, D.R., et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chong, C.Y., et al., Radiology Clinic North American 7, 3319 (1969).
Cuttone, G., "Applications of a Particle Accelerators in Medical Physics" Istituto Nazionale di Fisica Nucleare-Laboratori Nazionali del Sud, V.S. Sofia, 44 Cantania, Italy (17 pages).
Flanz, et al., "Large Medical Gantries", 1995 Particle Accelerator Conference, Massachusetts General Hospital, pp. 1-5 (1995).
Flanz, et al., "The Northeast Proton Therapy Center at Massachusetts General Hospital", Fifth Workshop on Heavy Charge Particles in Biology and Medicine, GSI, Darmstadt (Aug. 1995).
Fukumoto, "Cyclotron Versus Synchrotron for Proton Beam Therapy", KEK Prepr., No. 95-122, pp. 533-536 (1995).
Goto, A. et al., "Progress on the Sector Magnets for the Riken SRC," American Institute of Physics, CP600, Cyclotrons and Their Applications 2001, Sixteenth International Conference (2001), pp. 319-323.
Graffman, S., et al., Acta Radiol. Therapy Phys. Biol. 9, 1 (1970).
Ishibashi, K. and McInturff, A., "Stress Analysis of Superconducting 10T Magnets for Synchrotron", Proceedings of the Ninth International Cryogenic Engineering Conference, pp. 513-516 (May 11-14, 1982).
Kanai, et al., "Three-dimensional Beam Scanning for Proton Therapy," Nuclear Instruments and Methods in Physic Research, Sep. 1, 1983, The Netherlands, vol. 214, No. 23, pp. 491-496.
Karlin, D.L., et al., "Medical Radiology" (Moscow) 28, 13 (1983).
Karlin, D.L., et al., "The State and Prospects in the Development of the Medical Proton Tract on the Synchrocyclotron in Gatchina", Med. Radiol., Moscow, vol. 28(3), pp. 28-32 (Mar. 1983)(German with English Abstract on end of p. 32).
Kim, J.W., "An Eight Tesla Superconducting Magnet for Cyclotron Studies," Ph.D. Dissertation, Michigan State University, Department of Physics and Astronomy (1994).
Kim, J., et al., "Construction of 8T Magnet Test Stand for Cyclotron Studies", *IEEE Transactions on Applied Superconductivity*, vol. 3, No. 1, pp. 266-268 (Mar. 1993).
Kim, J., et al., "Design Study of a Superconducting Cyclotron for Heavy Ion Therapy", *Cyclotrons and Their Applications 2001, Sixteenth International Conference*, pp. 324-326 (May 13-17, 2001).
Kim, J. and Blosser, H., "Optimized Magnet for a 250 MeV Proton Radiotherapy Cyclotron", Cyclotrons and Their Applications 2001, *Sixteenth International Conference*, pp. 345-347 (May 2001).
Kim, J.W., et al., "Trim Coil System for the Riken Cyclotron Ring Cyclotron",*Proceedings of the 1997 Particle Accelerator Conference, IEEE*, vol. 3, pp. 214-235 (Dec. 1981). OR 3422-3424, 1998).

Kraft, G. et al., "Hadrontherapy in Oncology", U. Amaldi and Larrsson, editors Elsevier Science, 1994.
Krevet, et al, "Design of a Strongly Curved Superconducting Bending Magnet for a Compact Synchrotron Light Source", Advances in Cryogenic Engineering, vol. 33, pp. 25-32.
Larsson, B., et al., Nature 182, 1222 (1958).
Lawrence, J.H., Cancer 10, 795 (1957).
Lawrence, J.H., et al., "Heavy particles in acromegaly and Cushing's Disease," in Endocrine and Norendocrine Hormone Producing Tumors (Year Book Medical Chicago, 1973), pp. 29-61.
Lawrence, J.H., et al., "Successful Treatment of Acromegaly: Metabolic and Clinical Studies in 145 Patients", The Journal of Clinical Endrocrinology and Metabolism, vol. 31, No. 2, Aug. 1970.
Lawrence, J.H., et al., Treatment of Pituitary Tumors, (Excerpta medica, Amsterdam/American Elsevier, New York, 1973), pp. 253-262.
Linfoot, J.A., et al., "Acromegaly," in Hormonal Proteins and Peptides, edited by C.H. Li, (1975), pp. 191-246.
Literature Author and Keyword Search, Feb. 14, 2005 (44 pages).
Literature Author and Keyword Searches (Synchrotron), Jan. 25, 2005 (78 pages).
Marti, F., et al., "High Intensity Operation of a Superconducting Cyclotron", *Proceedings of the 14the International Conference, Cyclotrons and Their Applications*, pp. 45-48 (Oct. 1995).
Moser, H.O., et al., "Nonlinear Beam Optics with Real Fields in Compact Storage Rings", Nuclear Instruments & Methods in Physics Research/Section B, B30, Feb. 1988, No. 1, pp. 105-109.
National Cancer Institute Funding (Senate-Sep. 21, 1992) (www.thomas.loc.gov/cgi-bin/query/z?r102:S21SE2-712 (2 pages).
Nolen, J.A., et al., "The Integrated Cryogenic—Superconducting Beam Transport System Planned for MSUI", *Proceedings of the 12th International Conference on High-Energy Accelerators*, pp. 549-551 (Aug. 1983).
Pourrahimi, S. et al., "Powder Metallurgy Processed Nb3Sn(Ta) Wire for High Field NMR magnets," IEEE Transactions on Applied Superconductivity, vol. 5, No. 2, (Jun. 1995), pp. 1603-1606.
Research & Development Magazine, "Proton Therapy Center Nearing Completion", vol. 41, No. 9, Aug. 1999 (2 pages)(www.rdmag.com).
Salzburger, H., et al., "Superconducting Synchrotron Magnets Supraleitende Synchrotronmagnete", Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schneider et al., "Superconducting Cyclotrons," IEEE Transactions on Magnetics, vol. MAG-11, No. 2, Mar. 1975, New York, pp. 443-446.
Schneider, R., et al., "Nevis Synchrocyclotron Conversion Program—RF System," *IEEE Transactions on Nuclear Science USA ns* 16(3) pp. 430-433 (Jun. 1969).
Stanford, A.L., et al., "Method of Temperature Control in Microwave Ferroelectric Measurements," Sperry Microwave Electronics Company, Clearwater, Florida, Sep. 19, 196 (1 page).
Superconducting Cyclotron Contract awarded by Paul Scherrer Institute (PSI), Villigen, Switzerland, http://www.accel.de/News/superconducting_cyclotron_contract.html.
Tadashi, I., et al., "Large superconducting super collider (SSC) in the planning and materials technology", vol. 78, No. 8 (19920801), pp. 1305-1313, The Iron and Steel Institute of Japan 00211575.
Takada, Yoshihisa Tsukumba, "A review of rotating gantries for heavy charged particle therapy," Symposium of Research Center for Charged Particle Therapy on Fundamental development of the charged particle therapy, Chiba (Japan), Nov. 13-14, 2001.
Takayama, T., et al., "Compact Cyclotron for Proton Therapy," *Proceedings of the 8th Symposium on Accelerator Science and Technology* , Japan (Nov. 25-27, 1991) pp. 380-382.
"The Davis 76-Inch Isochronous Cyclotron", Beam on: Crocker Nuclear Laboratory, University of California.
The Journal of Practical Pharmacy, vol. 46, No. 1, 1995, pp. 97-103. [Japanese].
Tobias, C.A., et al., Cancer Research 18, 121 (1958).

Toyoda, E., "Proton Therapy System", Sumitomo Heavy Industries, Ltd.

Tsuji, H., "Cancer Therapy by Proton Beam: Latest State and Future Prospects", *Isotope News*, No. 459, pp. 2-7 (1992).

Vorobiev, L.G., et al., "Concepts of a Compact Achromatic Proton Gantry with a Wide Scanning Field", Nuclear Instruments and Methods in Physics Research, Section A., vol. 406, No. 2, pp. 307-310 (1998).

Wikipedia, "Cyclotron" http://en.wikipedia.org/wiki/Cyclotron (originally visited Oct. 6, 2005, revisited Jan. 28, 2009)(7 pages).

Wikipedia, "Synchrotron" http://en.wikipedia.org/wiki/Synchrotron (originally visited Oct. 6, 2005, revisited Jan. 28, 2009)(7pages).

Worldwide Patent Assignee Search, Jan. 24, 2005 (224 pages).

Wu, X., "Conceptual Design and Orbit Dynamics in a 250 MeV Superconducting Synchrocyclotron," Ph.D. Dissertation, Michigan State University, Department of Physics and Astronomy (1990).

York, R.C., et al., "Present Status and Future Possibilities at NSCL-MSU", EPAC 94, Fourth European Particle Accelerator Conference, pp. 554-556 (Jun. 1994).

York, R.C., et al., "The NSCL Coupled Cyclotron Project—Overview and Status", *Proceedings of the Fifteenth International Conference on Cyclotrons and their Applications*, pp. 687-691 (Jun. 1998).

Zherbin, E. A., et al., "Proton Beam Therapy at the Leningrad Synchrocyclotron (Clinicomethodological Aspects and Therapeutic Results)", pp. 17-22, Aug. 1987, vol. 32(8)(German with English abstract on pp. 21-22).

18th Japan Conference on Radiation and Radioisotopes [Japanese], Nov. 25-27, 1987, 9 pages.

"510(k) Summary: Ion Beam Applications S.A.", FDA, Apr. 13, 2001.

"510(k) Summary: Optivus Proton Beam Therapy System", Jul. 21, 2000, 5 pages.

C/E Source of Ions for Use in Sychro-Cyclotrons Search, Jan. 31, 2005, 9 pages.

Source Search Cites of U.S. and Foreign Patents/Published applications in the name of Mitsubishi Denki Kabushiki Kaisha and Containing the Keywords (Proton and Synchrocyclotron), 8 pages.

European Search Report from application No. EP 06838033.6 (PCT/US2006/044853) mailed May 11, 2009 (69 pages).

European response filed in corresponding European application No. EP06838033.6, filed with the European Patent Office on Feb. 15, 2010 (14 pages).

Chinese foreign associate corresponding regarding Chinese office action with proposed amendments to claims for corresponding Chinese application No. 200680051421.0 mailed Dec. 25, 2009 (7 pages).

Chinese office action issued in corresponding Chinese application No. 200680051421.0 mailed Dec. 25, 2009 with English translation (8 pages).

Abstract and English machine translation of German Patent No. DE4411171(A1) (5 pages).

English abstract of DE4411171 from Chinese office action in corresponding Chinese application No. 200680051421.0 mailed Dec. 25, 2009 (1 page).

\* cited by examiner

CHARGED PARTICLE RADIATION THERAPY

This application is entitled to the benefit of the filing date of U.S. provisional patent application Ser. No. 60/738,404, filed Nov. 18, 2005, the entire text of which is incorporated by reference here.

BACKGROUND

This description relates to charged particle (e.g., proton or ion) radiation therapy.

The energy of a proton or ion beam for therapy needs to be high compared to the energy of an electron beam used in conventional radiotherapy. A proton beam, for example, that has a residual range of about 32 cm in water is considered adequate to treat any tumor target in the human population. When allowance is made for the reduction in residual range that results from scattering foils used to spread the beam, an initial proton beam energy of 250 MeV is needed to achieve the residual range of 32 cm.

Several kinds of particle accelerators can be used to produce a 250 MeV proton beam at a sufficient beam current (e.g., about 10 nA) for radiotherapy, including linear accelerators, synchrotrons, and cyclotrons.

The design of a proton or ion radiation therapy system for a clinical environment should take account of overall size, cost, and complexity. Available space is usually limited in crowded clinical environments. Lower cost allows more systems to be deployed to reach a broader patient population. Less complexity reduces operating costs and makes the system more reliable for routine clinical use.

Other considerations also bear on the design of such a therapy system. By configuring the system to apply the treatment to patients who are held in a stable, reproducible position (for example, lying supine on a flat table), the physician can more precisely relocate the intended target, relative to the patient's anatomy, at each treatment. Reliable reproduction of the patient's position for each treatment also can be aided using custom molds and braces fitted to the patient. With a patient in a stable, fixed position, the radiotherapy beam can be directed into the patient from a succession of angles, so that, over the course of the treatment, the radiation dose at the target is enhanced while the extraneous radiation dose is spread over non-target tissues.

Traditionally, an isocentric gantry is rotated around the supine patient to direct the radiation beam along successive paths that lie at a range of angles in a common vertical plane toward a single point (called an isocenter) within the patient. By rotating the table on which the patient lies around a vertical axis, the beam can be directed into the patient along different paths. Other techniques have been used to vary the position of the radiation source around the patient, including robotic manipulation. And other ways to move or reposition the patient have been used.

In high energy x-ray beam therapy, the x-ray beam may be directed toward the isocenter from an electron linear accelerator mounted on the gantry or robotic arm.

In typical proton beam therapy, the circular particle accelerator that produces the beam is too large to mount on the gantry. Instead, the accelerator is mounted in a fixed position and the particle beam is redirected through a rotating gantry using magnetic beam steering elements. Blosser has proposed to mount an accelerator on the side of the gantry near the horizontal axis of rotation.

SUMMARY

In general, in one aspect, an accelerator is mounted on a gantry to enable the accelerator to move through a range of positions around a patient on a patient support. The accelerator is configured to produce a proton or ion beam having an energy level sufficient to reach any arbitrary target in the patient from positions within the range. The proton or ion beam passes essentially directly from the accelerator housing to the patient.

Implementations may include one or more of the following features. The gantry is supported for rotation on bearings on two sides of the patient support. The gantry has two legs extending from an axis of rotation and a truss between the two legs on which the accelerator is mounted. The gantry is constrained to rotate within a range of positions that is smaller than 360 degrees, at least as large as 180 degrees and in some implementations in the range from about 180 degrees to about 330 degrees. (A rotation range of 180 degrees is sufficient to provide for all angles of approach into a supine patient.) Radio-protective walls include at least one wall that is not in line with the proton or ion beam from the accelerator in any of the positions within the range; that wall is constructed to provide the same radio-protection with less mass. The patient support is mounted in an area that is accessible through a space defined by a range of positions at which the gantry is constrained not to rotate. The patient support is movable relative to the gantry including rotation about a patient axis of rotation that is vertical. The patient axis of rotation contains an isocenter in the vicinity of a patient on the patient support. The gantry axis of rotation is horizontal and contains the isocenter. The accelerator weighs less than 40 Tons and in typical implementations within a range from 5 to 30 tons, occupies a volume of less than 4.5 cubic meters and typically in a range from 0.7 to 4.5 cubic meters, and produces a proton or ion beam having an energy level of at least 150 MeV and in a range from 150 to 300 MeV, for example 250 MeV.

The accelerator can be a synchrocyclotron with a magnet structure that has a field strength of at least 6 Tesla and can be from 6 to 20 Tesla. The magnet structure includes superconducting windings that are cooled by cryo-coolers. The proton or ion beam passes directly from the accelerator to the general area of the patient stand. A shielding chamber containing the patient support, the gantry, and the accelerator includes at least one wall of the chamber being thinner than other walls of the chamber. A portion of the chamber can be embedded within the earth.

In general, in one aspect, an accelerator is configured to produce a proton or ion beam having an energy level sufficient to reach any arbitrary target in a patient. The accelerator is small enough and lightweight enough to be mounted on a rotatable gantry in an orientation to permit the proton or ion beam to pass essentially directly from the accelerator housing to the patient.

In general, in one aspect, a medical synchrocyclotron has a superconducting electromagnetic structure that generates a field strength of at least 6 Tesla, produces a beam of particles, such as protons, having an energy level of at least 150 MeV, has a volume no larger than 4.5 cubic meters, and has a weight less than 30 Tons.

In general, in one aspect, a patient is supported within a treatment space, a beam of proton or ions pass in a straight line direction from an output of an accelerator to any arbitrary target within the patient, and the straight line direction is caused to be varied through a range of directions around the patient.

In general, in an aspect, a structure includes a patient support and a gantry on which an accelerator is mounted to enable the accelerator to move through a range of positions around a patient on the patient support. The accelerator is configured to produce a proton or ion beam having an energy level sufficient to reach any arbitrary target in the patient from positions within the range. A walled enclosure contains the patient support, the gantry, and the accelerator. In some examples, more than half of the surface of the walled enclosure is embedded within the earth.

Other aspects include other combinations of the aspects and features discussed above and other features expressed as apparatus, systems, methods, software products, business methods, and in other ways.

By generating a magnetic field of about 10 Tesla, the size of the accelerator approaches 1.5 meter and the mass is reduced to about 15 to 20 tons. The weight will depend on the stray magnetic field that is to be allowed near the accelerator. Even smaller weights and sizes may be possible. This enables the cyclotron to be placed on a gantry, with the output beam aimed directly at the isocenter, and rotated around the patient, thus simplifying the delivery of proton or ion beam radiation therapy. All extracted beam focusing and steering elements are incorporated into the accelerator or immediately adjacent to it. The direct mounting of the accelerator on the gantry eliminates beam transport elements that would otherwise be required to transport the beam from the accelerator to the target volume within the patient. The size, complexity and cost of a proton or ion beam therapy system are reduced and its performance is improved. Reducing the range of rotation of the gantry to be less than 360 degrees in the vertical plane reduces the thickness of the shielding barrier that must be provided at locations to which the beam is never directed. It also allows for ease of access to the patient treatment space. The synchrocyclotron can be scaled to arbitrarily high fields without compromising beam focusing during acceleration. The elimination of cryogenic liquid cooled coils reduces the risk to the operator and the patient if vaporized liquid cryogen were to be released during a fault condition such as a magnet quench.

Other advantages and features will become apparent from the following description and from the claims.

DETAILED DESCRIPTION

Figure 1:
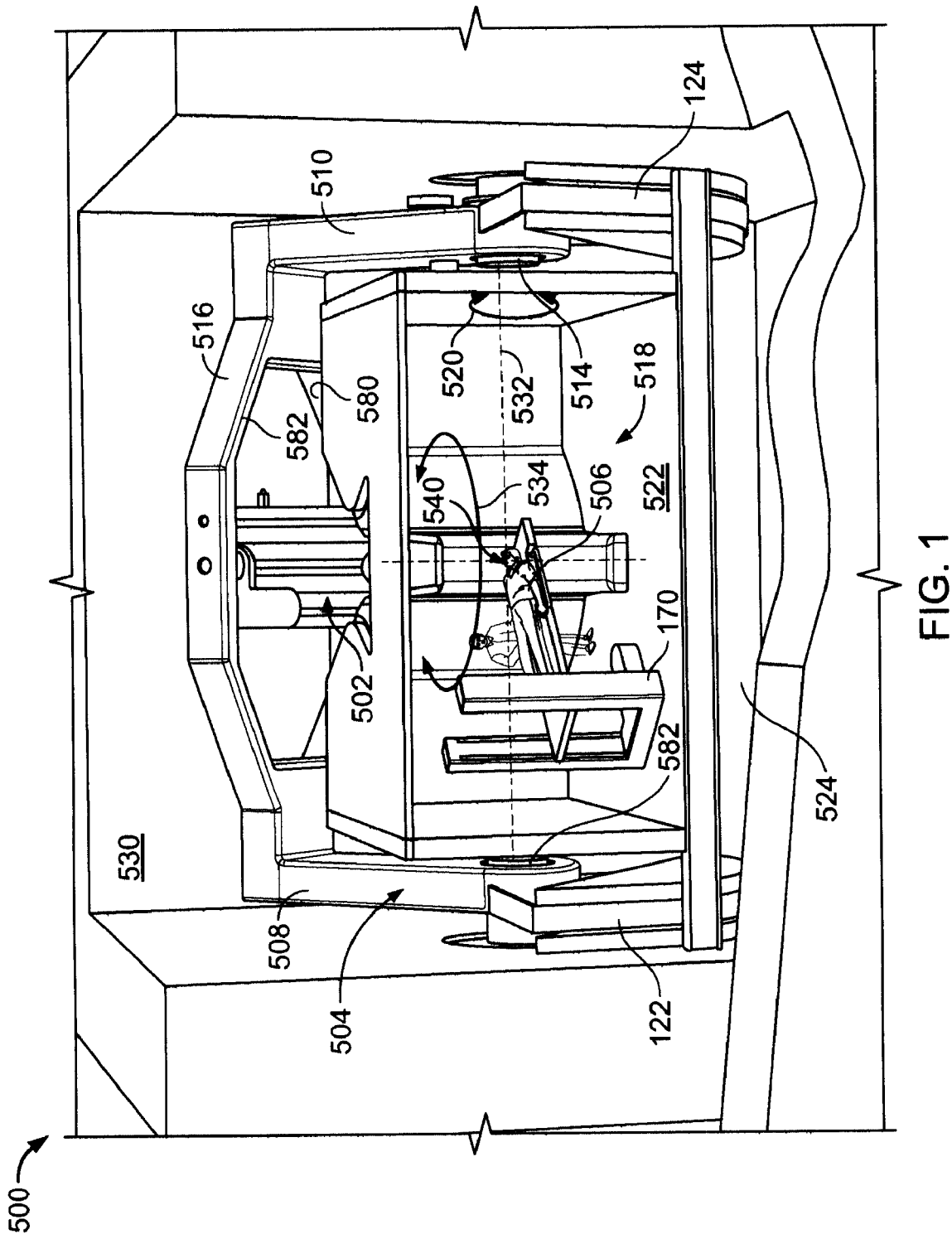
FIG. 1 is a perspective view of a therapy system.
Figure 2:
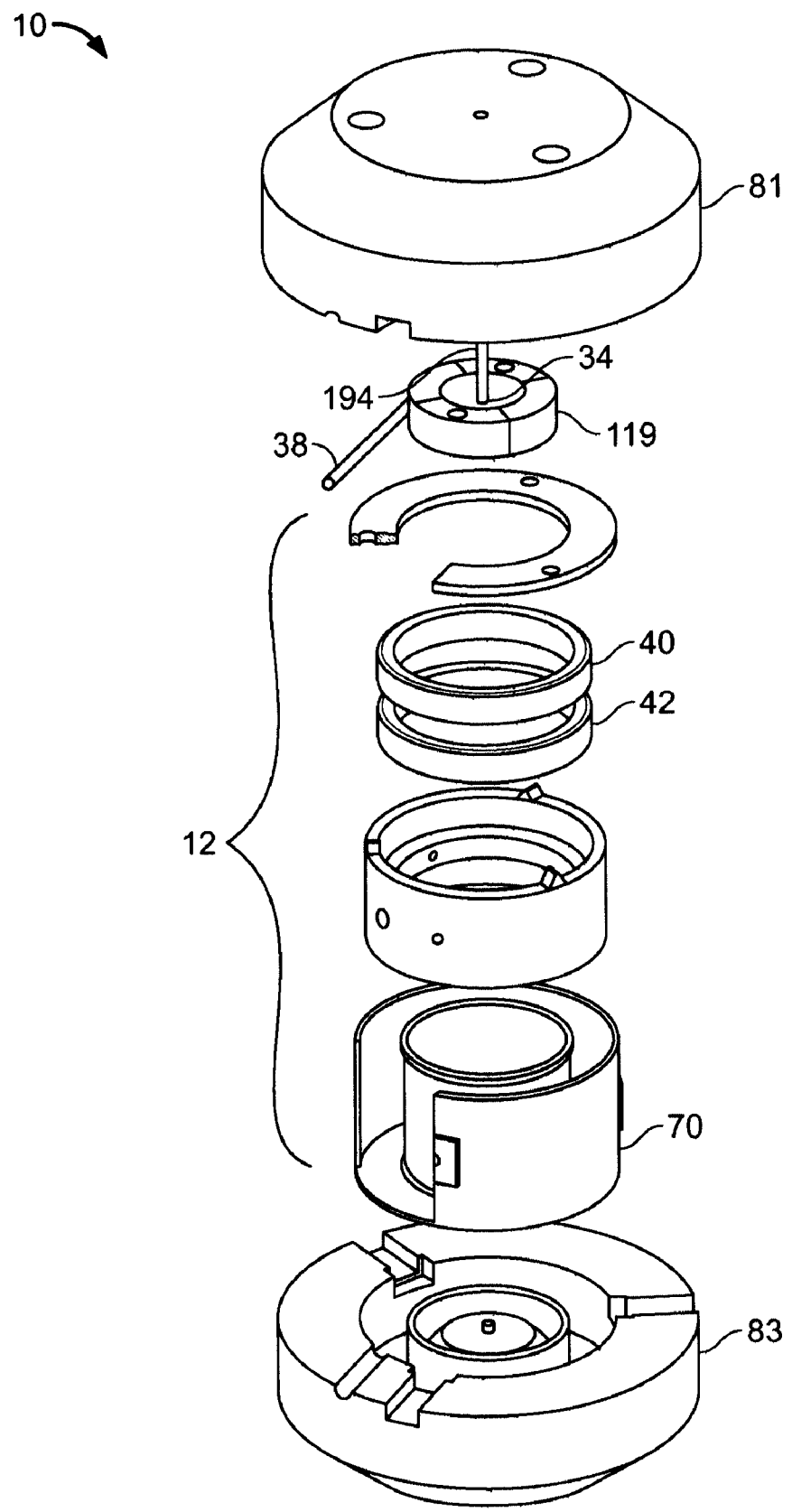
FIG. 2 is an exploded perspective view of components of a synchrocyclotron.

As shown in FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506. The size and cost of the therapy system are significantly reduced and the reliability and precision of the system may be increased.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls (which never directly receive the beam, e.g., wall 530) which provide radiation shielding of people outside the treatment area. A range of 180 degrees of gantry rotation is enough to cover all treatment approach angles, but providing a larger range of travel can be useful. For example the range of rotation may usefully be between 180 and 330 degrees and still provide clearance for the therapy floor space. When the range of travel is large, the gantry may swing to positions that are hazardous to people or equipment positioned in a portion of the therapy space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter.

For an average magnetic field strength larger than about 5 Tesla, an isochronous cyclotron (in which the magnet is constructed to make the magnetic field stronger near the circumference than at the center to compensate for the mass increase and maintain a constant frequency of revolution) is impractical to use to achieve 250 MeV protons. This is because the angular variation in magnetic field used to maintain the beam focus in the isochronous cyclotron cannot be made large enough using iron pole face shaping.

The accelerator described here is a synchrocyclotron. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Certain superconducting materials begin to lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers, rather than bath cooling the windings in liquid Helium, reduces complexity and cost.

The synchrocyclotron is supported on the gantry so that the beam is generated directly in line with the patient. The gantry permits rotation of the cyclotron about a horizontal rotational axis that contains a point (isocenter 540) within or near the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam needs to be about twice as thick as a wall at the opposite end of the room to provide an equivalent level of protection. Limiting the range of gantry rotation enables the treatment room to be sited below earth grade on three sides while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 6 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (502 in FIG. 1) includes a magnet system 12 that contains an ion source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figure 7:
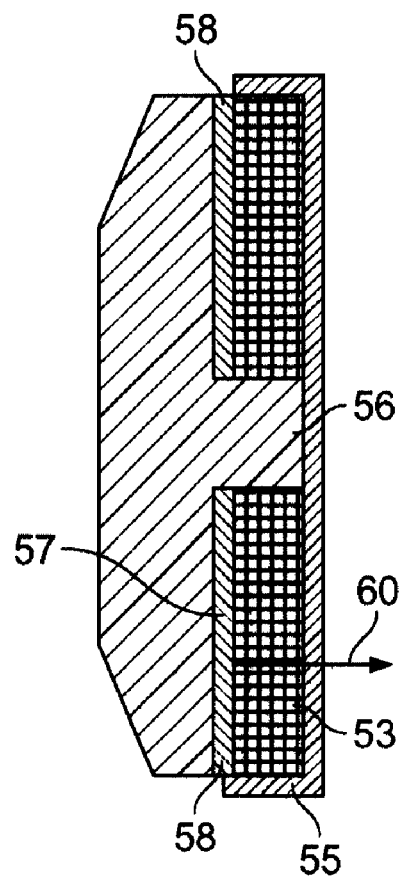
FIG. 7 is a cross-sectional view of a portion of a reverse bobbin and windings.
Figure 8:
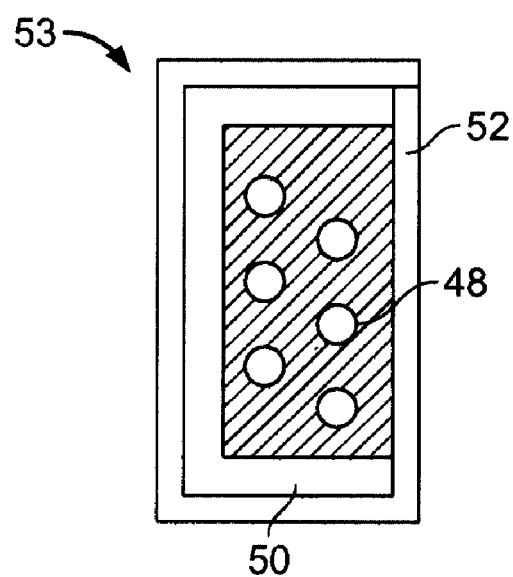
FIG. 8 is a cross sectional view of a cable-in-channel composite conductor.

The two superconducting magnet coils are centered on a common axis 47 and are spaced apart along the axis. As shown in FIGS. 7 and 8, the coils are formed by of Nb3Sn-based superconducting 0.6 mm diameter strands 48 (that initially comprise a niobium-tin core surrounded by a copper sheath) deployed in a Rutherford cable-in-channel conductor geometry. After six individual strands are laid in a copper channel 50, they are heated to cause a reaction that forms the final (brittle) material of the winding. After the material has been reacted, the wires are soldered into the copper channel (outer dimensions 3.02×1.96 mm and inner dimensions 2.05× 1.27 mm) and covered with insulation 52 (in this example, a woven fiberglass material). The copper channel containing the wires 53 is then wound in a coil having a rectangular cross-section of 6.0 cm×15.25 cm, having 30 layers and 47 turns per layer. The wound coil is then vacuum impregnated with an epoxy compound 54. The finished coils are mounted on an annular stainless steel reverse bobbin 56. A heater blanket 55 is held against the inner face of the bobbin and the windings to protect the assembly in the event of a magnet quench. In an alternate version the superconducting coil may be formed of 0.8 mm diameter Nb3Sn based strands. These strands can be deployed in a 4 strand cable, heat treated to form the superconducting matrix and soldered into a copper channel of outer dimension 3.19 by 2.57 mm. The integrated cable in channel conductor can be insulated with overlapped woven fiberglass tape and then wound into coils of 49 turns and 26 layers deep with a rectangular cross section of 79.79 mm by 180.5 mm and inner radius of 374.65 mm. The wound coil is then vacuum impregnated with an epoxy compound. The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at room temperature (20 degrees C.) can achieve this.

The geometry of the coil is maintained by mounting the coils in a "reverse" rectangular bobbin 56 and incorporating a pre-compression stainless steel bladder 58 between each coil and an inner face 57 of the bobbin to exert a restorative force 60 that works against the distorting force produced when the coils are energized. The bladder is pre-compressed after the coils and the heater blanket are assembled on the bobbin, by injecting epoxy into the bladder and allowing it to harden. The precompression force of the bladder is set to minimize the strain in the brittle Nb3Sn superconducting matrix through all phases of cool-down and magnet energizing.

Figure 5:
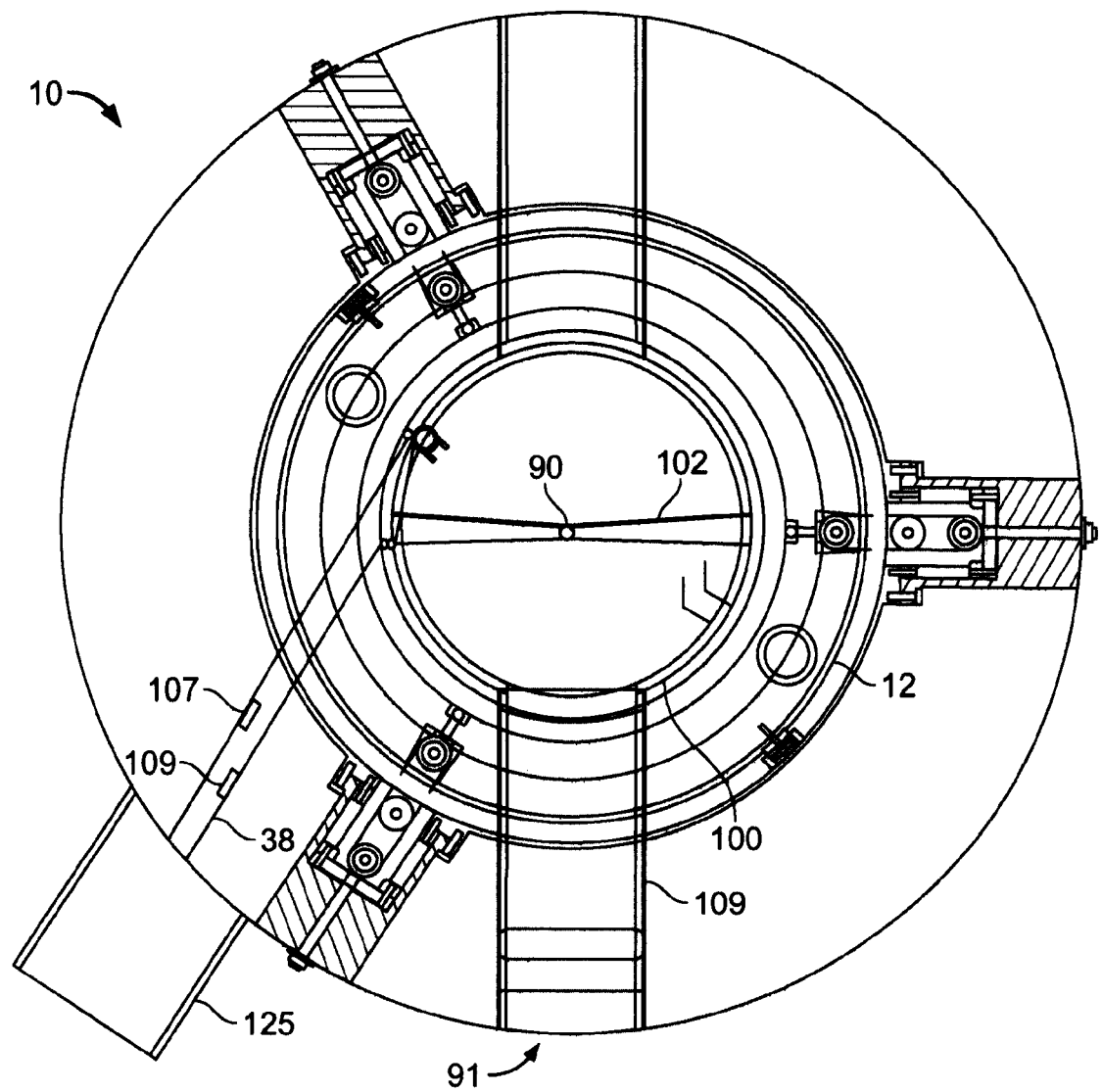
Figure 6:
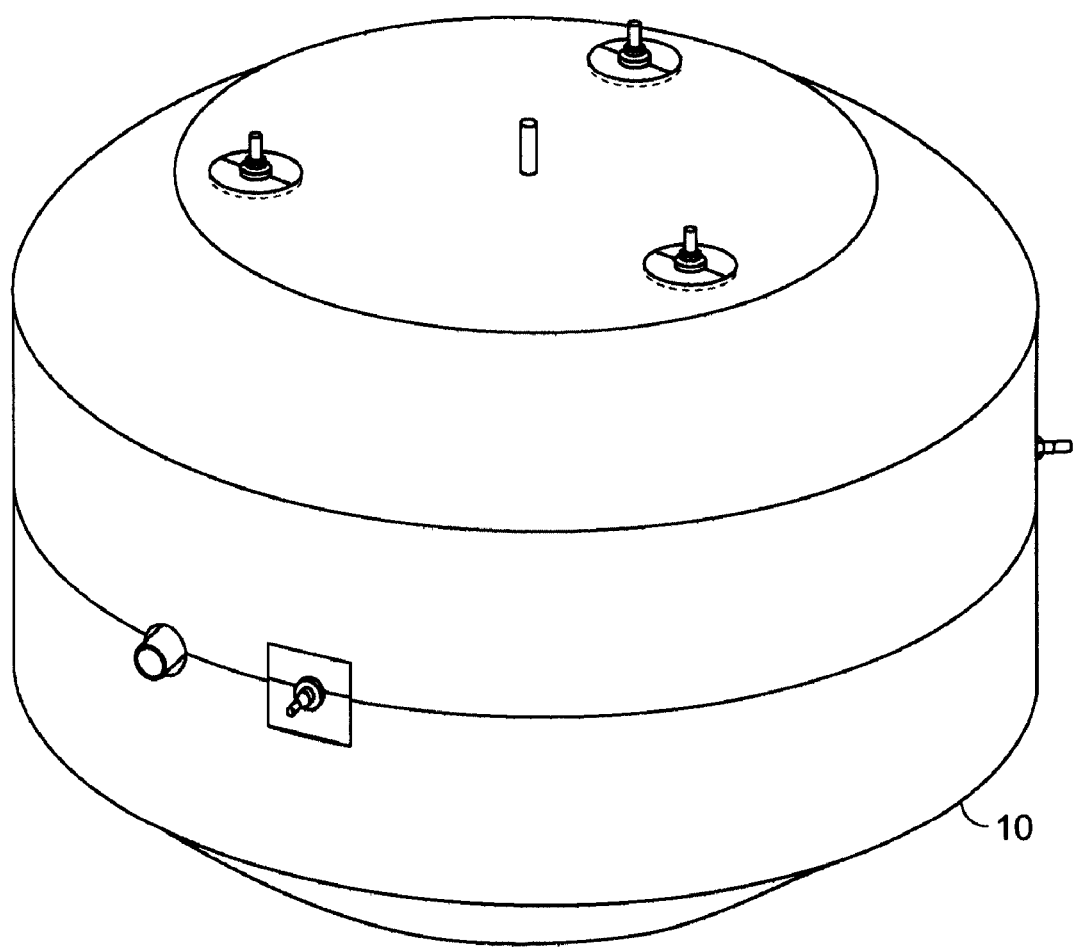
FIG. 6 is a perspective view of a synchrocyclotron.

As shown in FIG. 5, the coil position is maintained relative to the magnet yoke and cryostat using a set of warm-to-cold support straps 402, 404, 406. Supporting the cold mass with thin straps minimizes the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to minimize the dynamic forces imparted on the coil as the gantry accelerates and decelerates when the position is changed. Each warm-to-cold support includes 3 S2 fiberglass links. Two links 410, 412 are supported across pins between the warm yoke and an intermediate temperature (50-70 K), and one link 408 is supported across the intermediate temperature pin and a pin attached to the cold mass. Each link is 10.2 cm long (pin center to pin center) and is 20 mm wide. The link thickness is 1.59 mm. Each pin is made of stainless steel and is 47.7 mm in diameter.

Figure 13:
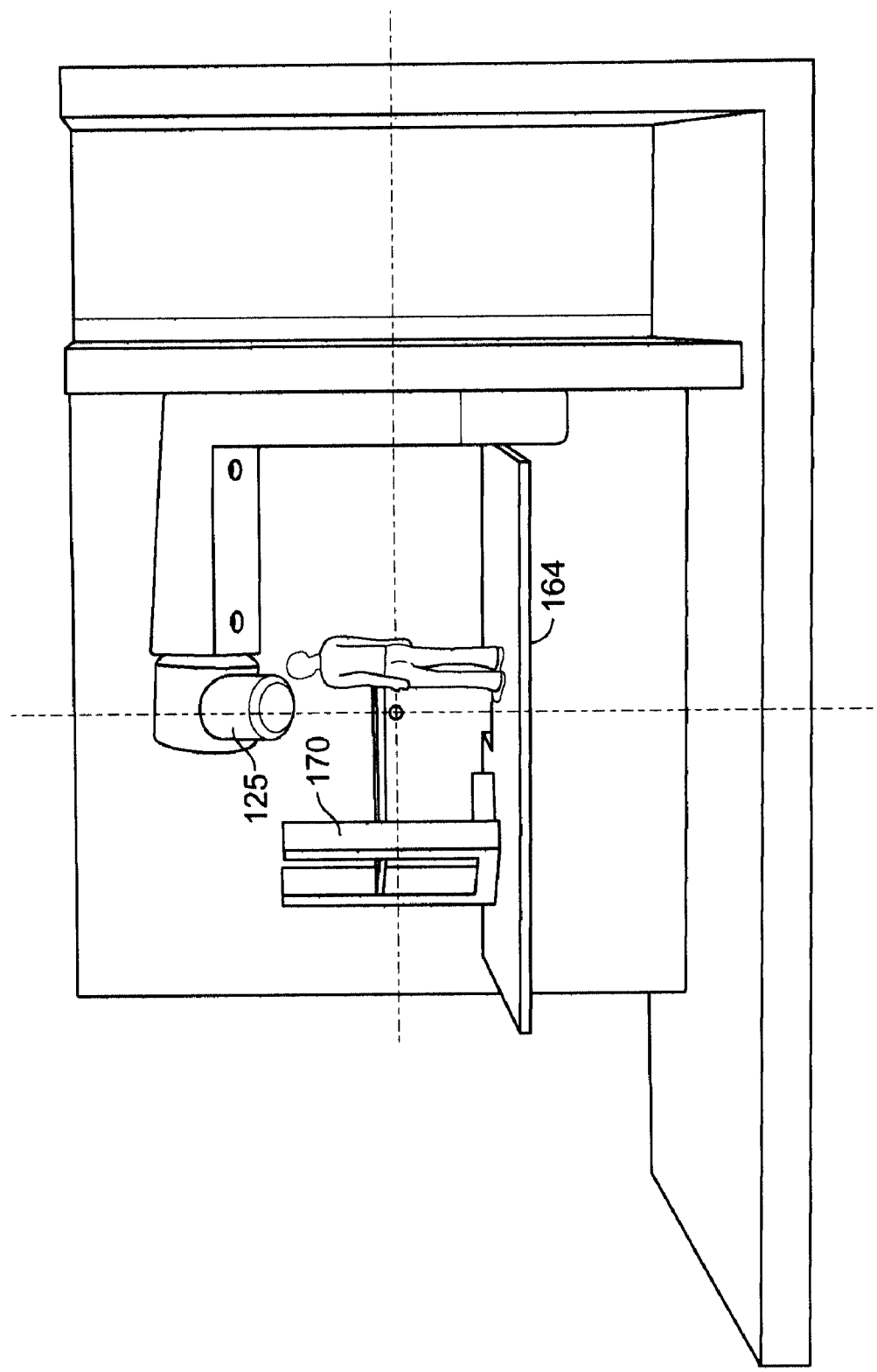
FIG. 13 shows a profile of one-half of a symmetrical profile of a pole face and a pole piece.

As shown in FIG. 13, the field strength profile as a function of radius is determined largely by choice of coil geometry; the pole faces 44, 46 of the permeable yoke material can be contoured to fine tune the shape of the magnetic field to insure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version the outer wall of the cryostat may be made of low carbon steel to provide an additional return flux path for the magnetic field. The temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads 81 that supply current to the superconducting windings.

The coil assembly and cryostatic chambers are mounted within and fully enclosed by two halves 81, 83 of a pillbox-shaped magnet yoke 82. In this example, the inner diameter of the coil assembly is about 140 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator.

Figure 3:
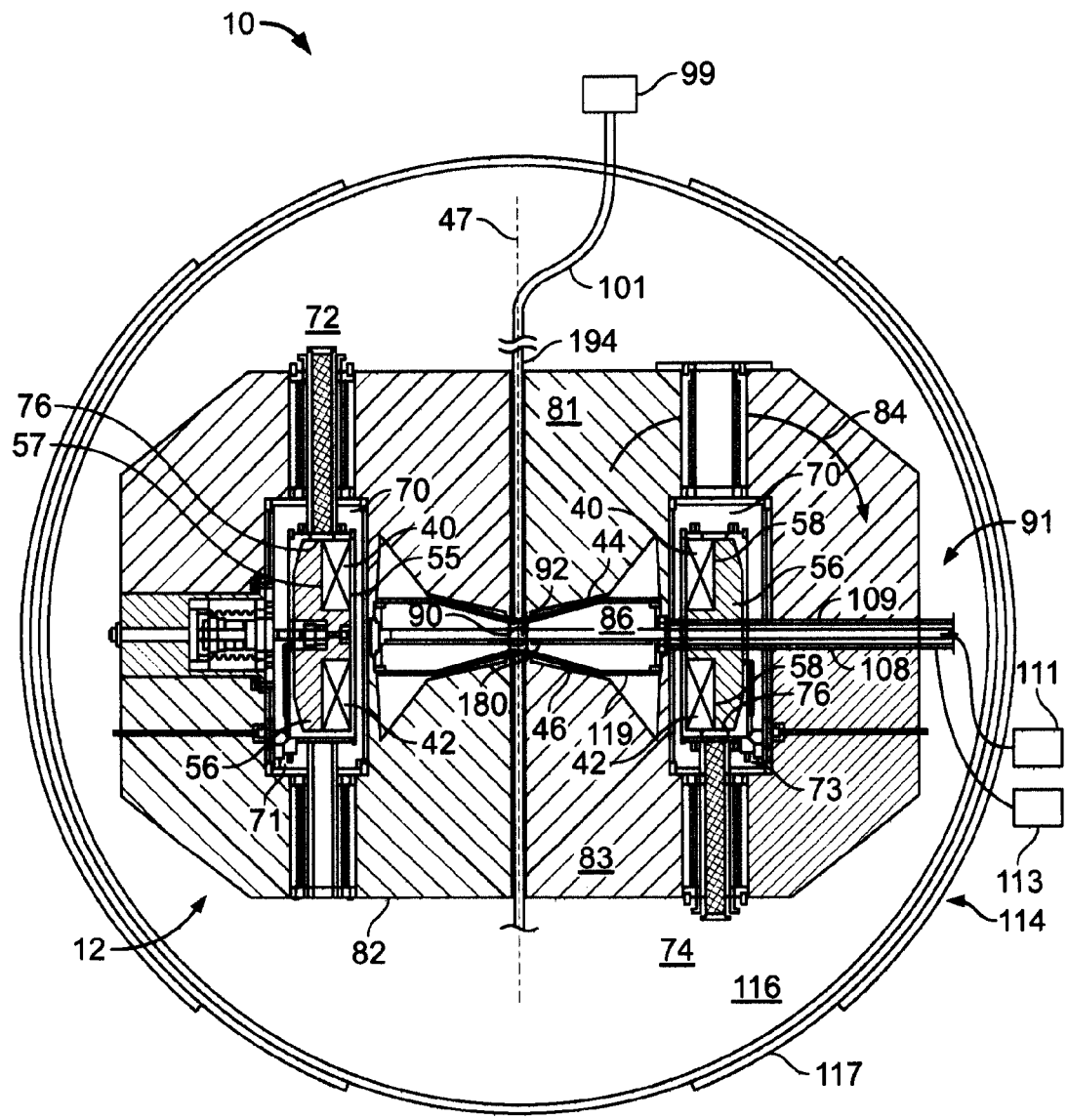
FIGS. 3, 4, and 5 are cross-sectional views of a synchrocyclotron.
Figure 4:
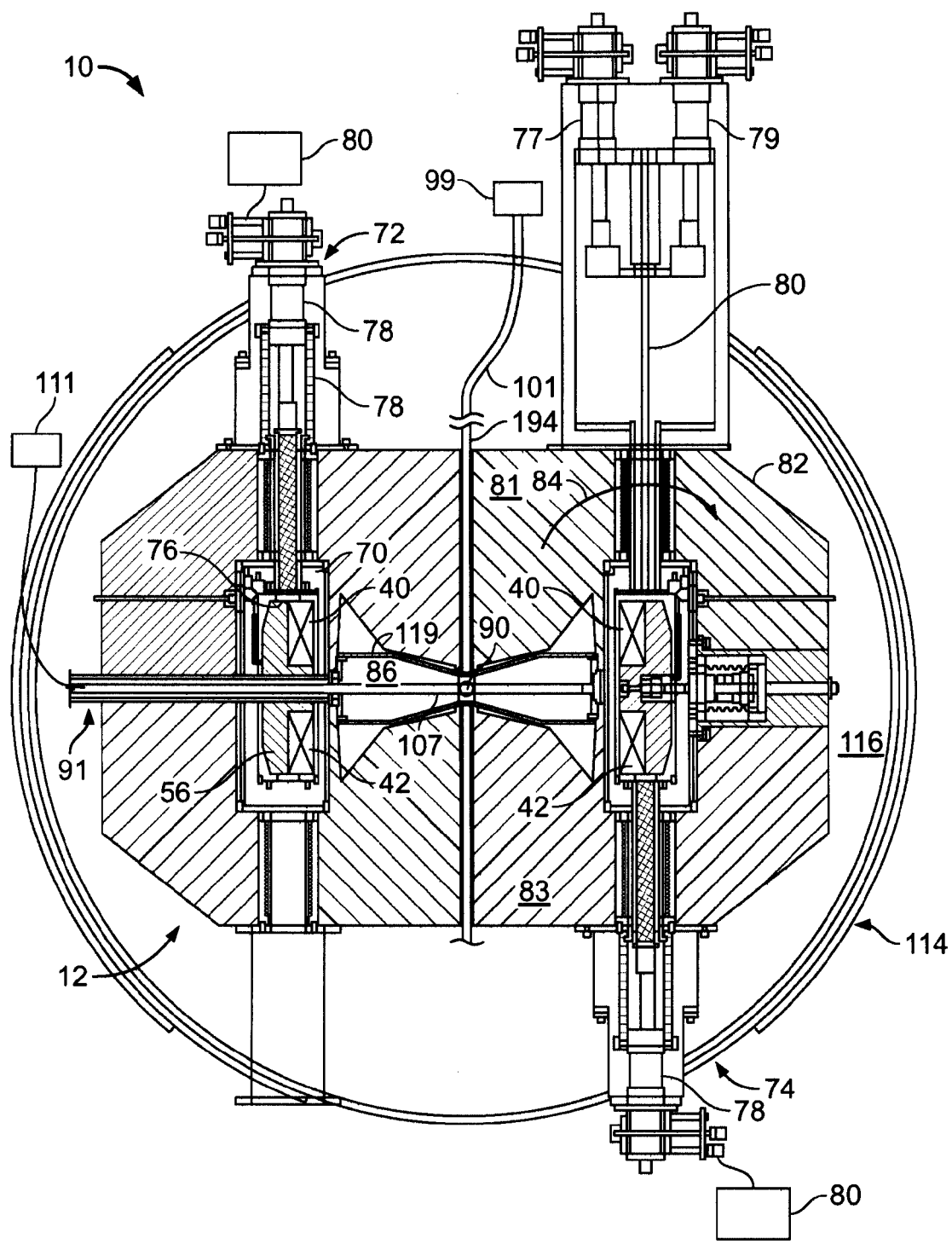
Figure 9:
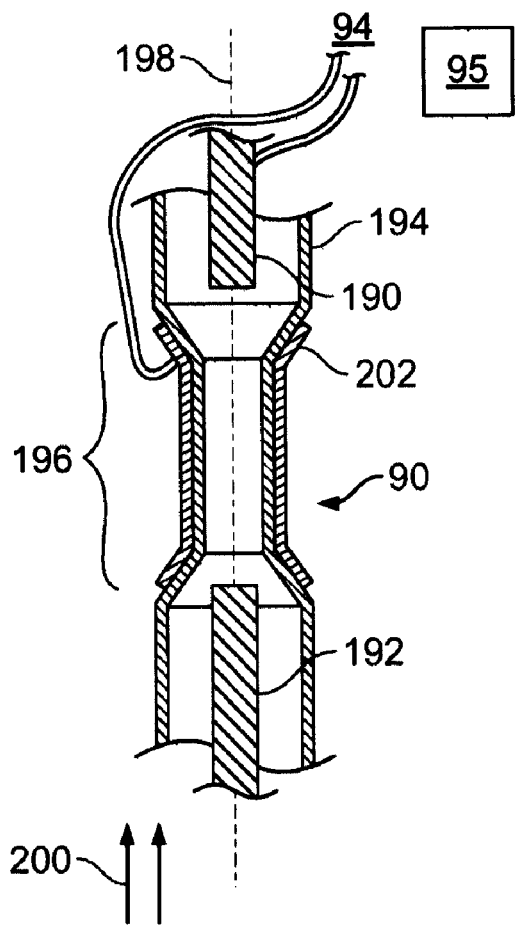
FIG. 9 is a cross-sectional view of an ion source.

As shown in FIGS. 3 and 9, the synchrocyclotron includes an ion source 90 of a Penning ion gauge geometry located near the geometric center 92 of the magnet structure 82. The ion source is fed from a supply 99 of hydrogen through a gas line 101 and tube 194 that delivers gaseous hydrogen. Electric cables 94 carry an electric current from a current source 95 to stimulate electron discharge from cathodes 192, 194 that are aligned with the magnetic field, 200.

Figure 10:
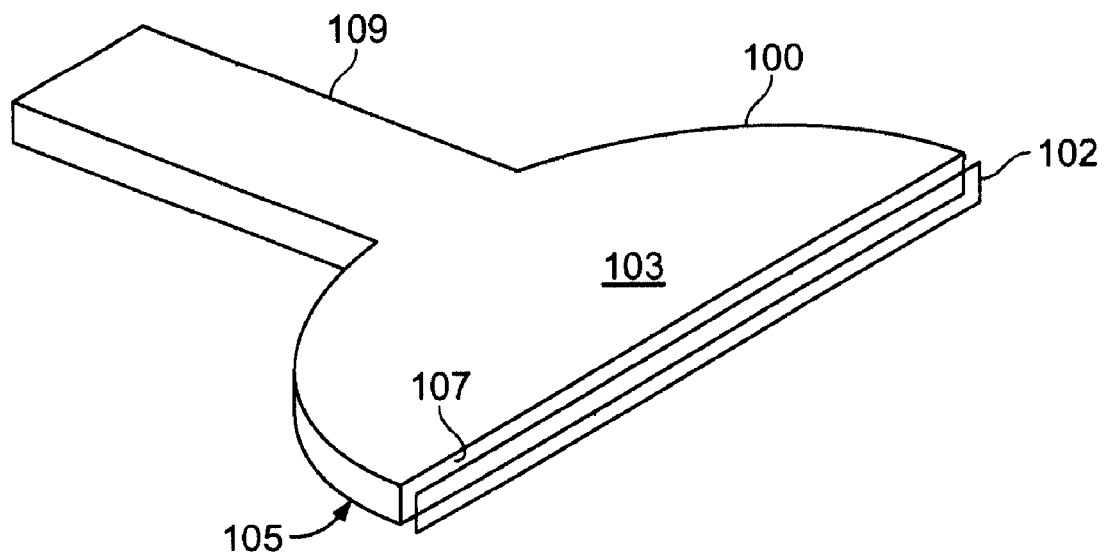
FIG. 10 is a perspective view of a dee plate and a dummy dee.

The discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radiofrequency electric field is made to vary in time as the accelerated particle beam increases in distance from the geometric center. Examples of radio frequency waveform generators that are useful for this purpose are described in U.S. patent application Ser. No. 11/187,633, titled "A Programmable Radio Frequency Waveform Generator for a Synchrocyclotron," filed Jul. 21, 2005,and in U.S. provisional patent application Ser. 60/590,089, same title, filed on Jul. 21, 2004,both of which are incorporated in their entirety by this reference.

For the beam emerging from the centrally located ion source to clear the ion source structure as it begins to spiral outward, a large voltage difference is required across the radiofrequency plates. 20,000 Volts is applied across the radiofrequency plates. In some versions from 8,000 to 20,000 Volts may be applied across the radiofrequency plates. To reduce the power required to drive this large voltage, the magnet structure is arranged to reduce the capacitance between the radio frequency plates and ground. This is done by forming holes with sufficient clearance from the radiofrequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

The vacuum chamber 119 in which the acceleration occurs is a generally cylindrical container that is thinner in the center and thicker at the rim. The vacuum chamber encloses the RF plates and the ion source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral path beginning at the ion source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38 to exit the yoke of the cyclotron. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

The magnetic field within the pole gap needs to have certain properties to maintain the beam within the evacuated chamber as it accelerates. The magnetic field index $$n = -(r/B)dB/dr$$

must be kept positive to maintain this "weak" focusing. Here r is the radius of the beam and B is the magnetic field. Additionally the field index needs to be maintained below 0.2, because at this value the periodicity of radial oscillations and vertical oscillations of the beam coincide in a $v_r = 2 v_z$ resonance. The betatron frequencies are defined by $v_r = (1-n)^{1/2}$ and $v_z = n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 that can be programmably controlled to create a desired combination of scattering angle and range modulation for the beam. Examples of beam forming systems useful for that purpose are described in U.S. patent application Ser. No. 10/949,734, titled "A Programmable Particle Scatterer for Radiation Therapy Beam Formation", filed Sep. 24, 2004, and U.S. provisional patent application Ser. No. 60/590,088, filed Jul. 21, 2005, both of which are incorporated in their entirety by this reference.

During operation, the plates absorb energy from the applied radio frequency field as a result of conductive resistance along the surfaces of the plates. This energy appears as heat and is removed from the plates using water cooling lines 108 that release the heat in a heat exchanger 113.

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one of the gantry legs and connected to the bearing housings by drive gears and belts or chains. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

All of the active systems of the synchrocyclotron (the current driven superconducting coils, the RF-driven plates, the vacuum pumps for the vacuum acceleration chamber and for the superconducting coil cooling chamber, the current driven ion source, the hydrogen gas source, and the RF plate coolers, for example), are controlled by appropriate synchrocyclotron control electronics (not shown).

The control of the gantry, the patient support, the active beam shaping elements, and the synchrocyclotron to perform a therapy session is achieved by appropriate therapy control electronics (not shown).

Figure 11:
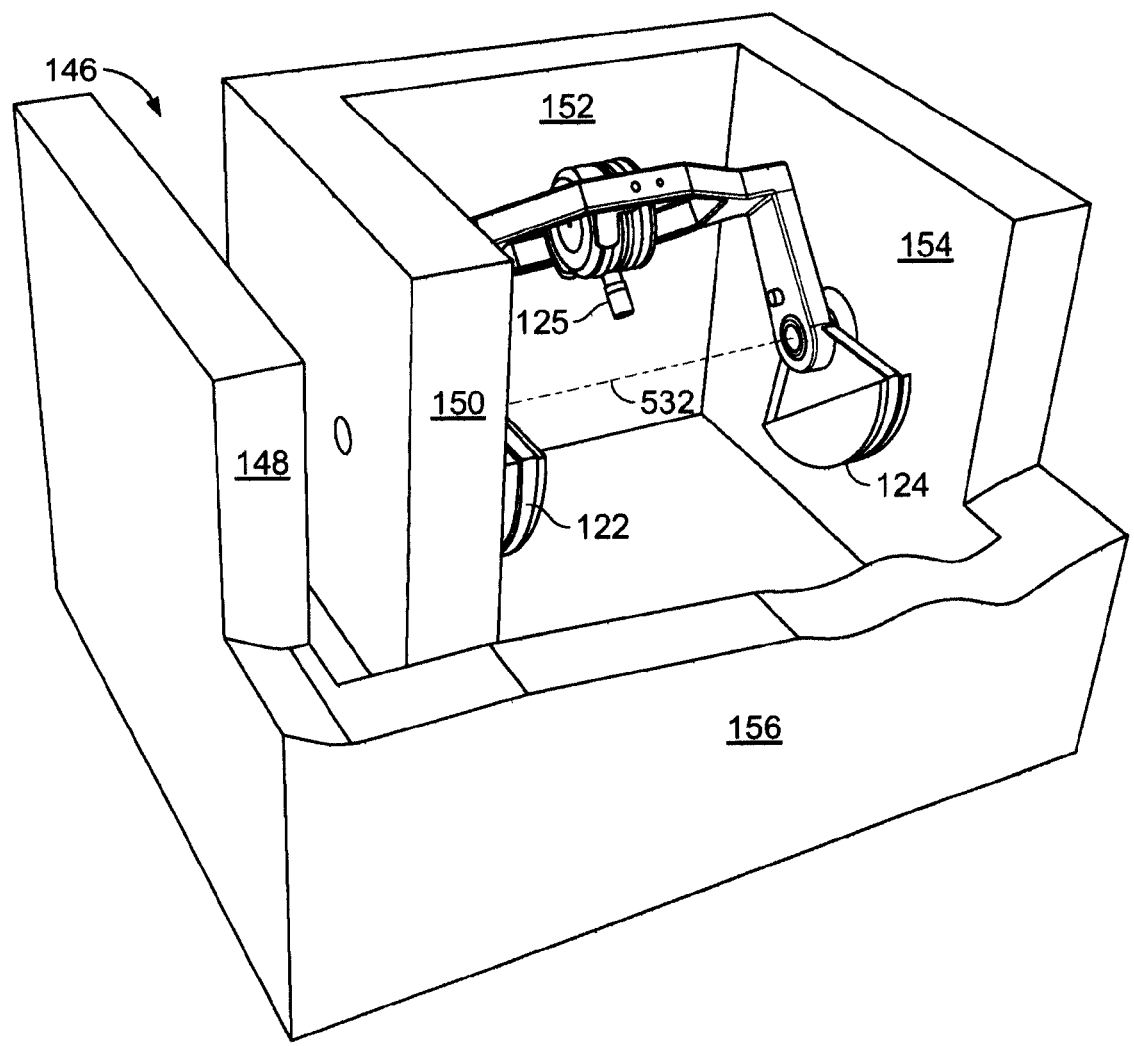
FIG. 11 is a perspective view of a vault.
Figure 12:
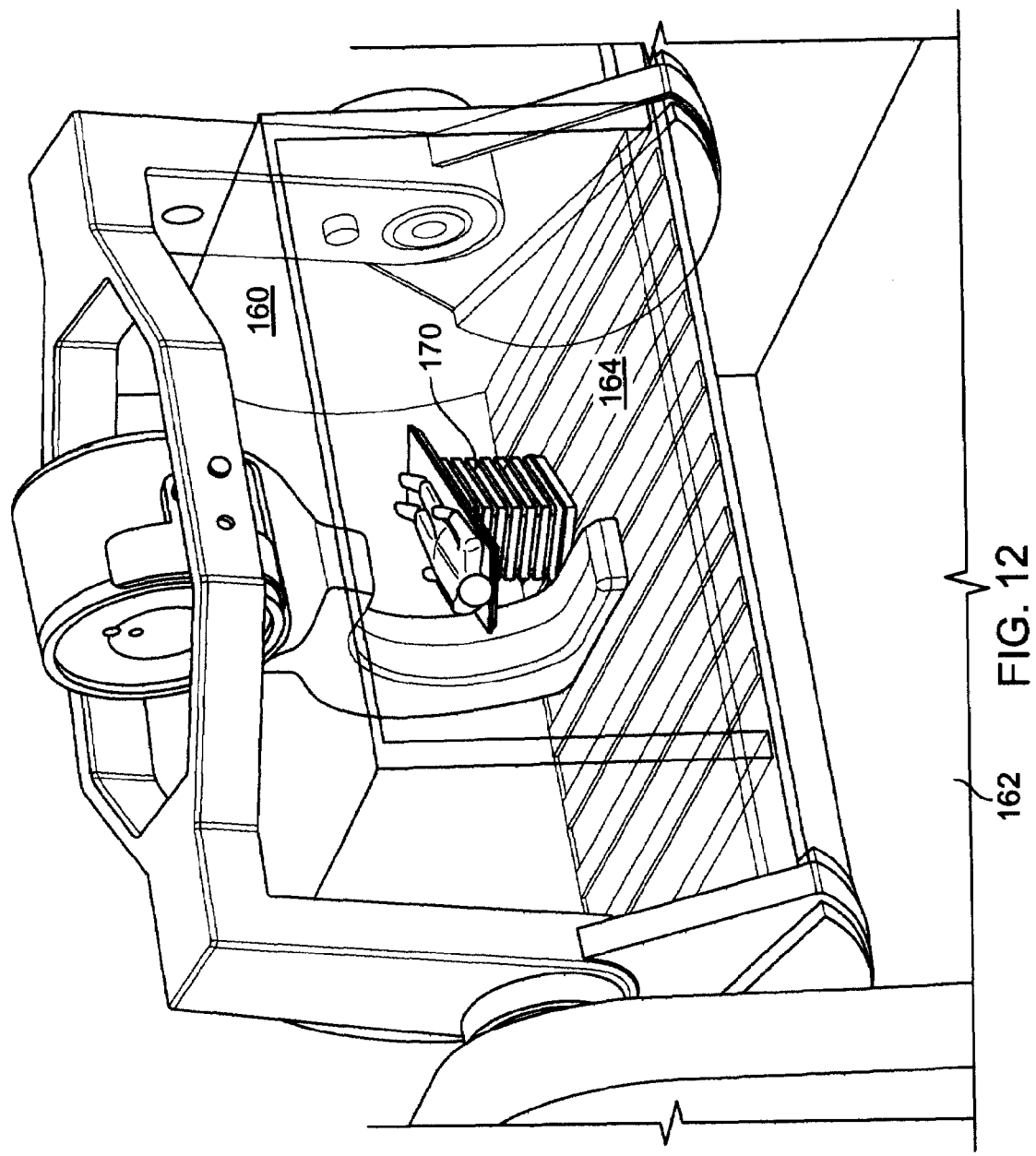
FIG. 12 is a perspective view of a treatment room with a vault.

As shown in FIGS. 1, 11, and 12, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is never in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

For safety and aesthetic reasons, a therapy room 160 is constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space.

Within the treatment room, the patient support 170 can be mounted in a variety of ways that permit the support to be raised and lowered and the patient to be rotated and moved to a variety of positions and orientations.

Additional information concerning the design of the accelerator can be found in U.S. provisional application Ser. No. 60/760,788, entitled HIGH-FIELD SUPERCONDUCTING SYNCHROCYCLOTRON (T. Antaya), filed Jan. 20, 2006, and U.S. patent application Ser. No. 11/463,402, entitled MAGNET STRUCTURE FOR PARTICLE ACCELERATION (T. Antaya, et al.), filed Aug. 9, 2006, and U.S. provisional application Ser. No. 60/850,565, entitled CRYOGENIC VACUUM BREAK PNEUMATIC THERMAL COUPLER (Radovinsky et al.), filed Oct. 10, 2006, all of which are incorporated in their entireties by reference here.

Other implementations are within the scope of the following claims.

What is claimed is:

1. An apparatus comprising
a patient support, and
a gantry on which an accelerator is mounted to enable the accelerator to move through a range of positions around a patient on the patient support,
the accelerator being configured to produce a proton or ion beam having an energy level sufficient to reach any arbitrary target in the patient from positions within the range,
the proton or ion beam passing essentially directly from an accelerator housing to the patient.

2. The apparatus of claim 1 in which the gantry is supported for rotation on two sides of the patient support.

3. The apparatus of claim 2 in which the gantry is supported for rotation on bearings on the two sides of the patient support.

4. The apparatus of claim 1 in which the gantry comprises two arms extending from an axis of rotation of the gantry and a truss between the two arms on which the accelerator is mounted.

5. The apparatus of claim 1 in which the gantry is constrained to rotate within a range of positions that is smaller than 360 degrees.

6. The apparatus of claim 5 in which the range is at least as large as 180 degrees.

7. The apparatus of claim 5 in which the range is from about 180 degrees to about 330 degrees.

8. The apparatus of claim 5 also including radio-protective walls, at least one of which is not in line with the proton or ion beam from the accelerator in any of the positions within the range, the one wall being constructed to provide the same radio-protection than the other walls with less mass.

9. The apparatus of claim 5 in which the patient support is mounted on a patient support area that is accessible through a space defined by a range of positions at which the gantry is constrained from rotation.

10. The apparatus of claim 1 in which the patient support is movable relative to the gantry.

11. The apparatus of claim 10 in which the patient support is configured for rotation about a patient axis of rotation.

12. The apparatus of claim 11 in which the patient axis of rotation is vertical.

13. The apparatus of claim 11 in which the patient axis of rotation contains an isocenter in a patient on the patient support.

14. The apparatus of claim 1 in which the patient gantry is configured for rotation of the accelerator about a gantry axis of rotation.

15. The apparatus of claim 14 in which the gantry axis of rotation is horizontal.

16. The apparatus of claim 14 in which the axis of rotation contains an isocenter in a patient on the patient support.

17. The apparatus of claim 1 in which the accelerator weighs less than 40 Tons.

18. The apparatus of claim 17 in which the accelerator weighs in a range from 5 to 30 Tons.

19. The apparatus of claim 1 in which the accelerator occupies a volume of less than 4.5 cubic meters.

20. The apparatus of claim 19 in which the volume is in the range of 0.7 to 4.5 cubic meters.

21. The apparatus of claim 1 in which the accelerator produces a proton or ion beam having an energy level of at least 150 MeV.

22. The apparatus of claim 21 in which the energy level is in the range from 150 to 300 MeV.

23. The apparatus of claim 1 in which the accelerator comprising a synchrocyclotron.

24. The apparatus of claim 1 in which the accelerator comprises a magnet structure having a field strength of at least 6 Tesla.

25. The apparatus of claim 24 in which the field strength is in the range of 6 to 20 Tesla.

26. The apparatus of claim 24 in which the magnet structure comprises superconducting windings.

27. The apparatus of claim 1 in which the proton or ion beam passes directly from the accelerator to the general area of the patient stand.

28. The apparatus of claim 1 also including a shielding chamber containing the patient support, the gantry, and the accelerator, at least one wall of the chamber being thinner than other walls of the chamber.

29. The apparatus of claim 28 in which at least a portion of the chamber is embedded within the earth.

30. An apparatus comprising
a medical synchrocyclotron having a superconducting electromagnetic structure that generates a field strength of at least 6 Tesla, produces, for delivery to a patient, a beam of charged particles having an energy level of at least 150 MeV, has a volume no larger than 4.5 cubic meters, and has a weight less than 30 Tons.

31. An apparatus comprising
an accelerator configured to produce a proton or ion beam having an energy level sufficient to reach any arbitrary target in a patient, the accelerator being small enough and lightweight enough to be mounted on a rotatable gantry in an orientation to permit the proton or ion beam to pass essentially directly from the accelerator to the patient.

32. The apparatus of claim 31 in which the accelerator comprises a superconducting synchrocyclotron.

33. A structure comprising
a patient support;
a gantry on which an accelerator is mounted to enable the accelerator to move through a range of positions around a patient on the patient support, the range of positions exceeding 180 degrees around the patient;
the accelerator being configured to produce a proton or ion beam having an energy level sufficient to reach any arbitrary target in the patient from positions within the range; and
a walled enclosure containing the patient support, the gantry, and the accelerator.

34. An apparatus comprising:
a patient support; and
a gantry on which an accelerator is mounted, the gantry being supported on two sides of the patient support for rotation (a) about a horizontal gantry axis that contains an isocenter in the patient and (b) through a range of positions that exceeds 180 degrees;
the patient support being rotatable about a vertical patient support axis that contains the isocenter;
the accelerator comprising a synchrocyclotron configured to produce a proton or ion beam having an energy level of at least 150 MeV to reach any arbitrary target in the patient directly from positions within the range, the synchrocyclotron having superconducting windings.

35. A method comprising
supporting a patient within a treatment space;
causing a beam of proton or ions to pass in a straight line direction from an output of an accelerator to any arbitrary target within the patient; and
causing the straight line direction to be varied through a range of positions around the patient, the range of positions exceeding 180 degrees around the patient.

36. An apparatus comprising
an accelerator configured to produce a charged particle beam and to be mounted on a gantry that enables the accelerator to move through a range of positions around a patient on a patient support, the range of positions exceeding 180 degrees around the patient;
the accelerator being configured to produce a charged particle beam having an energy level sufficient to reach any arbitrary target in the patient from positions within the range.

37. An apparatus comprising
a gantry configured to hold an accelerator and to enable the accelerator to move through a range of positions around a patient on a patient support, the range of positions exceeding 180 degrees around the patient; and
the accelerator being configured to produce a proton or ion beam having an energy level sufficient to reach any arbitrary target in the patient from positions within the range.

38. The apparatus of claim 32 in which the magnetic field of the superconducting synchrocyclotron is in the range of 6 to 20 Tesla.

39. The apparatus of claim 33 in which more than half of the surface of the walled enclosure is embedded within the earth.

* * * * *

UNITED STATES PATENT AND TRADEMARK OFFICE
CERTIFICATE OF CORRECTION

| | | |
|---|---|---|
| PATENT NO. | : 7,728,311 B2 | Page 1 of 1 |
| APPLICATION NO. | : 11/601056 | |
| DATED | : June 1, 2010 | |
| INVENTOR(S) | : Kenneth P. Gall | |

It is certified that error appears in the above-identified patent and that said Letters Patent is hereby corrected as shown below:

Column 11, line 57, in Claim 23, delete "comprising" and insert -- comprises --.

Signed and Sealed this

Twenty-fourth Day of August, 2010

David J. Kappos
*Director of the United States Patent and Trademark Office*